(12) United States Patent
Ceballos et al.

(10) Patent No.: US 11,197,893 B2
(45) Date of Patent: Dec. 14, 2021

(54) PURE PLATELET-RICH PLASMA (P-PRP) COMPOSITION FOR TREATMENT OF SUBCLINICAL MASTITIS AND METHODS OF PRODUCING AND USING THE SAME

(71) Applicant: Universidad de Caldas, Manizales (CO)

(72) Inventors: Alejandro Ceballos, Manizales (CO); Jorge U. Carmona, Manizales (CO)

(73) Assignee: Universidad de Caldas, Manizales (CO)

(*) Notice: Subject to any disclaimer, the term of this patent is extended or adjusted under 35 U.S.C. 154(b) by 0 days.

(21) Appl. No.: 15/345,563

(22) Filed: Nov. 8, 2016

(65) Prior Publication Data

US 2018/0125893 A1 May 10, 2018

(51) Int. Cl.

| | | |
|---|---|---|
| A61K 35/19 | (2015.01) | |
| A61K 35/15 | (2015.01) | |
| A61K 38/18 | (2006.01) | |
| A61K 38/19 | (2006.01) | |
| A61K 38/17 | (2006.01) | |
| A61K 31/194 | (2006.01) | |
| A61K 33/42 | (2006.01) | |
| A61K 31/7004 | (2006.01) | |
| A61K 31/52 | (2006.01) | |
| C12N 5/0787 | (2010.01) | |
| C12N 5/078 | (2010.01) | |

(52) U.S. Cl.
CPC ............ *A61K 35/19* (2013.01); *A61K 31/194* (2013.01); *A61K 31/52* (2013.01); *A61K 31/7004* (2013.01); *A61K 33/42* (2013.01); *A61K 35/15* (2013.01); *A61K 38/1725* (2013.01); *A61K 38/1841* (2013.01); *A61K 38/1858* (2013.01); *A61K 38/19* (2013.01); *C12N 5/0642* (2013.01); *C12N 5/0644* (2013.01)

(58) Field of Classification Search
CPC ...... A61K 35/19; A61K 31/194; A61K 31/52; A61K 31/7004; A61K 33/42; A61K 35/15; A61K 38/1725; A61K 38/1841; A61K 38/1858; A61K 38/19; A61K 47/02
See application file for complete search history.

(56) References Cited

U.S. PATENT DOCUMENTS

| | | | | |
|---|---|---|---|---|
| 6,890,728 B2 * | 5/2005 | Dolecek | ................. | A61K 35/19 435/2 |
| 8,221,745 B2 * | 7/2012 | Rosiello | ................... | A01N 1/00 424/93.72 |
| 2015/0056604 A1 * | 2/2015 | Sehgal | ................. | A01N 1/0215 435/2 |

OTHER PUBLICATIONS

Penniston et al. Quantitative Assessment of Citric Acid in Lemon Juice, Lime Juice, and Commercially-Available Fruit Juice Products. J. Endourol (2008), 7 page manuscript. (Year: 2008).*
Crawley et al. The central role of thrombin in hemostasis. Journal of Thrombosis and Haemostasis (2007), v5(suppl. 1), p. 95-101. (Year: 2007).*
Lopez et al. Temporal Bacteriostatic Effect and Growth Factor Loss in Equine Platelet Components and Plasma Cultured with Methicillin-Sensitive and Methicillin-Resistant *Staphylococcus aureus*: A Comparative In Vitro Study. Veterinary Medicine International (2014), Article ID 525826, 8 pages. (Year: 2014).*
BD product catalogue, (2014), 52 pages. (Year: 2014).*
Del Conde et al. Platelet activation leads to activation and propagation of the complement system. Journal of Experimental Medicine (2005), v201(6), p. 871-879. (Year: 2005).*
Lee et al. Platelet-Rich Plasma: Quantitative Assessment of Growth Factor Levels and Comparative Analysis of Activated and Inactivated Groups. Archives of Plastic Surgery (2013), v40, p. 530-535. (Year: 2013).*
Lange-Consiglio et al. Platelet concentrate in bovine reproduction: effects on in vitro embryo production and after intrauterine administration in repeat breeder cows. Reproductive Biology and Endocrinology (2015) 13:65. (Year: 2015).*
Teruflex® Blood Bag system (2012), 11 pages. (Year: 2012).*
Dhurat et al. Principles and Methods of Preparation of Platelet-Rich Plasma: A Review and Author's Perspective. J Cutan Aesthet Surg. Oct.-Dec. 2014; 7(4): 13 page reprint (Year: 2014).*
Silva et al. .Evaluation of the effect of calcium gluconate and bovine thrombin on the temporal release of transforming growth factor beta 1 and platelet-derived growth factor isoform BB from feline platelet isolates. BMC Veterinary Research (2012), 8:212, 7 pages. (Year: 2012).*
Sterile. (2014). In Collins Dictionaries (Ed.), Collins English Dictionary (12th ed.). London, UK: Collins. Retrieved from https://search.credoreference.com/content/entry/hcengdict/sterile/0?institutionId=743 (Year: 2014).*
Lam et al., Improving Bovine Udder Health: A national mastitis control program in the Netherlands,(2013), Journal of Dairy Science,vol. 96 No. 2, 1301-1311.
Ostensson et al, Prevalence of Subclinical Mastitis and Isolated Udder Pathogens in Dairy Cows in Southern Vietnam, (2013), Trop. Anim. Health Prod, 45: 979-986.
Saidi et al., Subclinical Mastitis in Cattle in Algeria: Frequency of Occurrence and Bacteriological Isolates, (2013) Journal of South African Veterinary Association, 84(1) Art.#929.
Reyes et al., Evaluation of the Efficacy of Intramuscular Versus Intramammary Treatment of Subclinical *Streptococcus agalactiae* Mastitis in Dairy Cows in Colombia, (2015), Journal of Dairy Science, vol. 98 No. 8, 5294-303.

(Continued)

*Primary Examiner* — Sean C. Barron
(74) *Attorney, Agent, or Firm* — The Morales Law Firm; Joseph L. Morales

(57) ABSTRACT

A pure platelet-rich plasma (P-PRP) composition as an alternative to conventional antibiotic treatment of subclinical mastitis caused by Gram-positive bacteria in bovine including five live platelets and leukocytes, an anticoagulant, and an activating substance.

11 Claims, 8 Drawing Sheets

(56) References Cited

OTHER PUBLICATIONS

Persson Waller et al., CNS Species and Antimicrobial Resistance in Clinical and Subclinical Bovine Mastitis, (2011) Elsevier Vet. Microbiol. 152(1-2): 112-16.
Nielsen et al., Economic Consequences of Mastitis and Withdrawal of Milk With High Somatic Cell Count in Swedish Dairy Herds, (2010) Animal 4(10) pp. 1758-1770.
Bexiga et al., Deterministic Model to Evaluate the Impact of Lactational Treatment of Subclinical Mastitis Due to Coagulase-Negative Staphylococci, (2011) Journal of Dairy Research, 78(3): 318-25.
De Vliegher et al., Invited Review: Mastitis in Dairy Heifers: Nature of the Disease, Potential Impact, Prevention, and Control, (2012) Journal of Dairy Science, vol. 95 No. 3, 1025-1040.
Schepers et al., Estimation of Variance Components for Somatic Cell Counts to Determine Thresholds for Uninfected Quarters, (1997) Journal Dairy Science, vol. 80 No. 8, 1833-40.
Dohoo et al., Diagnosing Intramammary Infections: Comparison of Multiple Versus Single Quarter Milk Samples for The Identification of Intramammary Infections In Lactating Dairy Cows, (2011) Journal of Dairy Science, vol. 94 No. 11, 5515-5522.
Malek Dos Reis et al., Evaluation of Somatic Cell Count Thresholds to Detect Subclinical Mastitis In Gyr Cows, (2011), Journal of Dairy Science, vol. 94 No. 9, 4406-4412.
Reyher and Dohoo, Diagnosing Intramammary Infections: Evaluation of Composite Milk Samples to Detect Intramammary Infections, (2011), Journal of Dairy Science, vol. 94 No. 7: 3387-3396.
Barlow, J., Mastitis Therapy and Antimicrobial Susceptibility: A Multispecies Review with a Focus on Antibiotic Treatment of Mastitis in Dairy Cattle, (2011) J. Mammary Gland Biol Neoplasia 16(4): 383-407.
Mazzilli and Zecconi, Assessment of Epithelial Cells' Immune and Inflammatory Response to *Staphylococcus aureus* When Exposed to a Macrolide, (2010) Journal of Dairy Research 77:404-10.
Giraldo et al. Effects of Sodium Citrate and Acid Citrate Dextrose Solutions on Cell Counts and Growth Factor Release From Equine Pure-Platelet Rich Plasma and Pure-Platelet Rich Gel, (2015) BMC Vet. Res. 11(60):015-0370.
Moojen et al., Antimicrobial Activity of Platelet-Leukocyte Gel Against *Staphylococcus aureus*, (2008) Journal of Orthopaedic Research. 26(3): 404-10.
Alvarez et al., In Vitro Bactericidal Activity of Equine Platelet Concentrates, Platelet Poor Plasma, and Plasma Against Methicillin-Resistant *Staphylococcus aureus*, (2011) Arch. Med. Vet. 43(2): 155-61.
Lopez et al., Temporal Bacteriostatic Effect and Growth Factor Loss in Equine Platelet Components and Plasma Cultured with Methicillin-Sensitive and Methicillin-Resistant *Staphylococcus aureus*: A Comparative In Vitro Study, (2014) Vet. Med. Int.525826(10): 24.
Lopez et al., Bacteriostatic Effect of Equine Pure Platelet-Rich Plasma and Other Blood Products Against Methicillin-Sensitive *Staphylococcus aureus*: An In Vitro Study, (2014), Vet. Comp. Orthop. Traumatol. 27(5): 372-78.
Lopez et al., Effect of Equine Leukocyte-Reduced Platelet Concentrates on Methicillin-Resistant *Staphylococcus aureus* Cultures and Measurement of Temporal Growth Factor Degradation, (2015), Elsevier Journal Equine Vet. Sci. 35(3): 219-224.
Yang et al., Antimicrobial Activity of Platelet-Rich Plasma and Other Plasma Preparations Against Periodontal Pathogens, (2014) Journal of Periodontology. 86(2): 310-18.
Li et al., Efficacy of Leukocyte- and Platelet-Rich Plasma Gel (L-PRP gel) in Treating Osteomyelitis in a Rabbit Model, (2012), J. Orthop. Res. 31(6): 949-56.
Li et al., Unique Antimicrobial Effects of Platelet-Rich Plasma and Its Efficacy as a Prophylaxis to Prevent Implant-Associated Spinal Infection, (2013) Advanced Healthcare Materials. 2(9):1277-84.
Burnouf et al., Antimicrobial Activity of Platelet (PLT)-Poor Plasma, PLT-Rich Plasma, PLT Gel, and Solvent/Detergent-Treated PLT Lysate Biomaterials Against Wound Bacteria, (2013) Transfusion 53(1):138-46.
Drago et al., Plasma Components and Platelet Activation are Essential for the Antimicrobial Properties of Autologous Platelet-Rich Plasma: An In Vitro Study, (2014) PLoS One 9(9).
Yeaman et al.,Modular Determinants of Antimicrobial Activity in Platelet Factor-4 Family Kinocidins, (2007) Elsevier Biochim. Biophys. Acta 1769 609-19.
Tohidnezhad et al., Platelets Display Potent Antimicrobial Activity and Release Human Beta-Defensin 2, (2012) Platelets 23(3): 217-223.
Mariani et al., Leukocyte Presence Does Not Increase Microbicidal Activity of Platelet-Rich Plasma In Vitro, (2015) BMC Microbiol. 15(149): 015-0482.
Dohan Ehrenfest et al., In Search of a Consensus Terminology in the Field of Platelet Concentrates for Surgical Use: Platelet-Rich Plasma (PRP), Platelet-Rich Fibrin (PRF), Fibrin Gel Polymerization and Leukocytes, (2012) Current Pharmaceutical Biotechnolgy 13(7): 1131-37.
Dohan Ehrenfest et al., Classification of Platelet Concentrates (Platelet-Rich Plasma-PRP, Platelet-Rich Fibrin-PRF) for Topical and Infiltrative Use in Orthopedic and Sports Medicine: Current Consensus, Clinical Implications and Perspectives, (2014) Muscles, Ligaments and Tendons Journal 4(1): 3-9.
Lange-Consiglio et al., Intramammary administration of platelet concentrate as an unconventional therapy in bovine mastitis: first clinical application, (2014) Journal of Dairy Science, 97(10):6223-30.
Piaggio et al., Reporting of Noninferiority and Equivalence Randomized trials: an extension of the CONSORT Statement (2006) JAMA 295(10):1152-60.
Carmona et al., Review of the currently available systems to obtain platelet related products to treat equine musculoskeletal injuries, (2013) Rec Pat Reg Med, 3:2. doi:10.2174/ 2210212700122882965.
Adkinson et al., "Implications of proposed changes in bulk tank somatic cell count regulations" (2001) Journal of Dairy Science. 84(2):370-374.
Dardik et al., Shear Stress-Stimulated Endothelial Cells Induce Smooth Muscle Cell Chemotaxis via Platelet-Derived Growth Factor-BB and Interleukin-I Alpha, (2005) Journal of Vascular Surgery. 41(2): 321-31.
Shigeta et al., Ovine Platelet Factor 4: Purification, Amino Acid Sequence, Radioimmunoassay and Comparison With Platelet Factor 4 of Other Species, (1991) Thrombosis Research 64(4): 509-520.
Lopez et al., Evaluation of a double centrifugation tube method for concentrating bovine platelets: cellular study, (2012) Arch Med Vet 44, 109-115.
Schukken et al., Noninferiority trial comparing a first generation cephalosporin with a third-generation cephalosporin in the treatment of Nonsevere Clinical Mastitis in Dairy Cows, (2013) Journal of Dairy Science vol. 96 No. 10, 6763-74.
Gutierrez et al., Study of a Two-Step Centrifugation Protocol for Concentrating Cells and Growth Factors in Bovine Platelet-Rich Plasma, (2017), Veterinary Medicine International, Article ID 1950401.
Giraldo et al., Effects of the breed, sex and age on cellular content and growth factor release from equine pure-platelet rich plasma and pure-platelet rich gel. (2013) BMC Vet Res. Feb. 12;9:29. doi: 10.1186/1746-6148-9-29.
Mazzucco et al., Not every PRP-gel is born equal. Evaluation of growth factor availability for tissues through four PRP-gel preparations: Fibrinet, RegenPRP-Kit, Plateltex and one manual procedure. (2009) Vox Sang. Aug.;97(2):110-8. doi:10.1111/j.1423-0410. 2009.01188.x.
Dohan et al. 2009. Classification of platelet concentrates: from pure platelet-rich plasma (P-PRP) to leucocyte- and platelet-rich fibrin (L-PRF). Trends in Biotechnology;27:158-167.
Giraldo et al. 2017. Influence of calcium salts and bovine thrombin on growth factor release from equine platelet-rich gel supernatants. VetCompOrthopTraumatol;30:1-7.
Jimenez-Aristizabal et al. 2017. Long-term cytokine and growth factor release from equine platelet-rich fibrin clots obtained with two different centrifugation protocols. Cytokine;97:149-155.
Palavecino et al. 2010. Bacterial contamination of platelets. Transfusion and Apheresis Science;42:71-82.
Sutter WW et al. Comparison of hematologic values and transforming growth factor-beta and insulin-like growth factor concentrations

(56) References Cited

OTHER PUBLICATIONS in platelet concentrates obtained by use of buffy coat and apheresis methods from equine blood. Am J Vet Res.2004.924-30.65(7).

Dragoo JL et al. Comparison of the acute inflammatory response of two commercial platelet-rich plasma systems in healthy rabbit tendons. Am J Sports Med. 2012. 1274-81.40(6).

Anitua E et al. Morphogen and proinflammatory cytokine release kinetics from PRGF-Endoret fibrin scaffolds: evaluation of the effect of leukocyte inclusion. J Biomed Mater Res A. 2015. 1011-20.103(3).

Komatsu DE et al.The In Vivo Impact of Leukocyte Injections on Normal Rat Achilles Tendons: Potential Detriment to Tendon Morphology, Cellularity, and Vascularity. Am J Orthop. 2018. 47(10) doi: 10.12788/ajo.2018.0085.

Oudelaar BW et al. Concentrations of Blood Components in Commercial Platelet-Rich Plasma Separation Systems: A Review of the Literature. Am J Sports Med. 2019. 479-487.47(2).

Kobayashi Y et al. Leukocyte concentration and composition in platelet-rich plasma (PRP) influences the growth factor and protease concentrations. J Orthop Sci. 2016. 683-689. 21(5).

Anitua, E, Plasma rich in growth factors: preliminary results of use in the preparation of future sites for implants. Int J Oral Maxillofac Implants, 1999. 14(4): p. 529-35.

Marx, RE., et al., Platelet-rich plasma: Growth factor enhancement for bone grafts. Oral Surg Oral Med Oral Pathol Oral Radiol Ended, 1998. 85(6): p. 638-46.

Marx, RE, Platelet-rich plasma (PRP): what is PRP and what is not PRP? Implant Dent, 2001. 10(4): p. 225-8.

Tambella, AM, et al., Platelet-rich Plasma and Other Hemocomponents in Veterinary Regenerative Medicine. Wounds, 2018. 30(11): p. 329-336.

Zimmermann, R., et al., Sample preparation technique and white cell content influence the detectable levels of growth factors in platelet concentrates. Vox Sang, 2003. 85(4): p. 283-9.

* cited by examiner

PURE PLATELET-RICH PLASMA (P-PRP) COMPOSITION FOR TREATMENT OF SUBCLINICAL MASTITIS AND METHODS OF PRODUCING AND USING THE SAME

FIELD OF THE INVENTION

The invention relates to improved control and treatment of mastitis without the use of antibiotics. Specifically, embodiments of the invention relate to therapeutic compositions and methods of obtaining and using the same, for treatment of subclinical mastitis produced by Gram-positive bacteria in mammals.

INCORPORATION BY REFERENCE

Any references (patent application publications, issued patents, or journal publications) cited in the present disclosure are also incorporated by reference herein in their entireties.

BACKGROUND

Mastitis is an inflammation of the udders caused by microorganisms that penetrate inside the mammary gland through the nipple to provoke a response of the immune system inside the mammary gland, thus causing physical, chemical, and bacteriological changes in the milk. Subclinical mastitis (SCM) is characterized by the absence of clinical signs related to the inflammation of the mammary gland, such as heat, redness, pain and edema. Such infections are usually associated with high somatic cell counts (SCC) and mammary pathogens (Lam et al., "Improving Bovine Udder Health: A national Mastitis Control Program in the Netherlands," J. Dairy Sci. 96(2): 1301-11 (2013)).

The most common bacteria isolations from cows with SCM are represented by Gram-positive pathogens (60% or more), such as *Staphylococcus aureus, Streptococcus uberis, Streptococcus dysgalactiae, Streptococcus agalactiae* and coagulase-negative *staphylococci* (Dos Reis et al. (2011); Ostensson et al., "Prevalence of Subclinical Mastitis and Isolated Udder Pathogens in Dairy Cows in Southern Vietnam," Trop. Anim Health Prod. 45(4): 979-86 (2013); Saidi et al., "Subclinical Mastitis in Cattle in Algeria: Frequency of Occurrence and Bacteriological Isolates," J. S. Afr. Vet. Assoc. 84(1):929 (2013); and Reyes et al., "Evaluation of the Efficacy of Intramuscular Versus Intramammary Treatment of Subclinical *Streptococcus agalactiae* Mastitis in Dairy Cows in Colombia," J. Dairy Sci. 98(8): 5294-303 (2015)), with the latter consisting of more than 45 different species and subspecies (Waller et al., "CNS Species and Antimicrobial Resistance in Clinical and Subclinical Bovine Mastitis," Vet. Microbiol. 152(1-2): 112-16 (2011); and De Vliegher et al. (2012)).

SCM is the most important cause of economic losses in the dairy cattle industry around the world (Nielsen et al., "Economic Consequences of Mastitis and Withdrawal of Milk With High Somatic Cell Count in Swedish Dairy Herds," Animal 4(10): 1758-70 (2010);Bexiga et al., "Deterministic Model to Evaluate the Impact of Lactational Treatment of Subclinical Mastitis Due to Coagulase-Negative *Staphylococci,"* J. Dairy Res. 78(3): 318-25 (2011); and De Vliegher et al., Invited Review: "Mastitis in Dairy Heifers: Nature of the Disease, Potential Impact, Prevention, and Control," J. Dairy Sci. 95(3): 1025-40 (2012)) Mammary health programs routinely include monitoring SCC to detect those apparently healthy cows that exhibits 1) increased SCC (Schepers et al., "Estimation of Variance Components for Somatic Cell Counts to Determine Thresholds for Uninfected Quarters," J. Dairy Sci. 80(8): 1833-40 (1997)), and 2) presence of pathogenic bacteria in milk (Dohoo et al., "Diagnosing Intramammary Infections: Comparison of Multiple Versus Single Quarter Milk Samples For The Identification of Intramammary Infections In Lactating Dairy Cows.," J. Dairy Sci. 94(11): 5515-22 (2011); Dos Reis et al., "Evaluation of Somatic Cell Count Thresholds to Detect Subclinical Mastitis In Gyr Cows," J. Dairy Sci. 94(9): 4406-12 (2011); Reyher and Dohoo, "Diagnosing Intramammary Infections: Evaluation of Composite Milk Samples to Detect Intramammary Infections," J. Dairy Sci. 94(7): 3387-96 (2011)).

Currently, the cornerstone treatment for SCM includes the use of antibiotic preparations (Barlow, J., "Mastitis Therapy and Antimicrobial Susceptibility: A Multispecies Review with a Focus on Antibiotic Treatment of Mastitis in Dairy Cattle," J. Mammary Gland Biol. Neoplasia 16(4): 383-407 (2011); Waller et al. (2011); and Reyes et al. (2015)). However, the use of antibiotics for the treatment of this disease remains as controversial due to the presence of antibiotic residuals in the milk and the development of bacterial resistance to antimicrobials among others (Barlow (2011)).

An element that must be taken into consideration in the case of mastitis, the goal is not only clinical healing but also having the choice of treatment with the best cost-benefit ratio, maximizing the production efficiency and not focusing exclusively on treatment effectiveness (Mazzilli and Zecconi, "Assessment of Epithelial Cells' Immune and Inflammatory Response to *Staphylococcus aureus* When Exposed to a Macrolide," J. Dairy Res. 77:404-10 (2010)). That is, the cost of mastitis stems not only from the qualitative-quantitative loss of milk that occurs during infection, but also from the interventions required every time a case of mastitis surfaces in the herd. Furthermore, it is particularly important to take into account the economic disadvantages deriving the use of antibiotics. The formulation is a readily available and cost-effective therapeutic agent that provides an alternative treatment of mastitis without the use of antibiotics.

Because of aforementioned concerns and to the fact that dairy farmers lose millions of dollars due to milk dumped during the antibiotic withdrawal, it is necessary to research and develop in different therapeutic strategies for SCM treatment (Barlow (2011)). In line with this, platelet-rich plasma (PRP) may be an alternative therapy for cows with SCM. Notably, PRP is an important source of growth factors (GFs), such as transforming growth factor beta 1 (TGF-$\beta_1$) and platelet derived growth factor (PDGF), among some other proteins necessary to induce wound healing and diminish inflammation (Giraldo et al., "Effects of Sodium Citrate and Acid Citrate Dextrose Solutions on Cell Counts and Growth Factor Release From Equine Pure-Platelet Rich Plasma and Pure-Platelet Rich Gel," BMC Vet. Res. 11(60): 015-0370 (2015)).

Furthermore, some in vitro (Moojen et al., "Antimicrobial Activity of Platelet-Leukocyte Gel Against *Staphylococcus aureus,"* J. Orthop. Res. 26(3): 404-10 (2008);Alvarez et al., "In Vitro Bactericidal Activity of Equine Platelet Concentrates, Platelet Poor Plasma, and Plasma Against Methicillin-Resistant *Staphylococcus aureus,"* Arch. Med. Vet. 43(2): 155-61 (2011); Lopez et al., "Temporal Bacteriostatic Effect and Growth Factor Loss in Equine Platelet Components and Plasma Cultured with Methicillin-Sensitive and Methicillin-Resistant *Staphylococcus aureus:* A Comparative In Vitro Study," Vet. Med. Int. 525826(10): 24 (2014a); Lopez et al., "Bacteriostatic Effect of Equine Pure Platelet-Rich Plasma and Other Blood Products Against Methicillin-Sensitive *Staphylococcus ureus*: An In Vitro Study," Vet. Comp. Orthop. Traumatol. 27(5): 372-78 (2014b); Lopez et al., "Effect of Equine Leukocyte-Reduced Platelet Concentrates on Methicillin-Resistant *Staphylococcus aureus* Cultures and Measurement of Temporal Growth Factor Degradation," J. Equine Vet. Sci. 35(3): 219-24 (2015); and Yang et al., "Antimicrobial Activity of Platelet-Rich Plasma and Other Plasma Preparations Against Periodontal Pathogens," J. Periodontol. 86(2): 310-18 (2015)) and in vivo (Li et al., "Efficacy of Leukocyte- and Platelet-Rich Plasma Gel (L-PRP gel) in Treating Osteomyelitis in a Rabbit Model," J. Orthop. Res. 31(6): 949-56. (2013a); and Li et al., "Unique Antimicrobial Effects of Platelet-Rich Plasma and Its Efficacy as a Prophylaxis to Prevent Implant-Associated Spinal Infection," Adv. Healthc. Mater. 2(9): 1277-84 (2013b)) studies have described an important bacteriostatic effect of this substance against several Gram-positive and Gram-negative bacteria, possibly through of plasma complement (Burnouf et al., "Antimicrobial Activity of Platelet (PLT)-Poor Plasma, PLT-Rich Rich Plasma, PLT Gel, and Solvent/Detergent-Treated PLT Lysate Biomaterials Against Wound Bacteria," Transfusion 53(1):138-46 (2013); and Drago et al., "Plasma Components and Platelet Activation are Essential for the Antimicrobial Properties of Autologous Platelet-Rich Plasma: An In Vitro Study, PLoS One 9(9) (2014)) and some chemokines released during platelet activation, such as beta-defensin and platelet factor-4 (PF4) (Yeaman et al., "Modular Determinants of Antimicrobial Activity in Platelet Factor-4 Family Kinocidins," Biochim Biophys. Acta 3: 609-19 (2007); and Tohidnezhad et al., "Platelets Display Potent Antimicrobial Activity and Release Human Beta-Defensin 2," Platelets 23(3): 217-23 (2012)). Notably, it seems to be that the bacteriostatic effect described for several PRP preparations is not related to the concentrations of white blood cells (WBCs) in such hematologic products (Moojen et al. (2008); Lopez et al. (2014a); Lopez et al. (2014b); Lopez et al. (2015); and Mariani et al., "Leukocyte Presence Does Not Increase Microbicidal Activity of Platelet-Rich Plasma In Vitro," BMC Microbiol. 15(149): 015-0482 (2015)).

Currently, PRP for topical or infiltrative use (liquid preparations with an anticoagulant) is classified into two groups: 1) pure PRP (P-PRP) or leukocyte-poor PRP, which are preparations without leukocytes and with a low-density fibrin network after activation and; 2) leukocyte-PRP (L-PRP) products, which are preparations with leukocytes and a low-density fibrin network after activation (Dohan Ehrenfest et al., "In Search of a Consensus Terminology in the Field of Platelet Concentrates for Surgical Use: Platelet-Rich Plasma (PRP), Platelet-Rich Fibrin (PRF), Fibrin Gel Polymerization and Leukocytes," Curr. Pharm. Biotechnol. 13(7): 1131-37 (2012); and Dohan Ehrenfest et al., "Classification of Platelet Concentrates (Platelet-Rich Plasma-PRP, Platelet-Rich Fibrin-PRF) for Topical and Infiltrative Use in Orthopedic and Sports Medicine: Current Consensus, Clinical Implications and Perspectives," Muscles Ligaments Tendons J. 4(1): 3-9 (2014)).Once PRP preparations are activated, they are transformed into a platelet rich gel (PRG). Thus, the PRG from L-PRP is termed L-PRG, and the PRG from P-PRP is called P-PRG (Dohan Ehrenfest et al. (2012); Dohan Ehrenfest et al. (2014)).

Italian researchers recently found that an allogeneic platelet lysate was useful to treat cows with both acute and chronic clinical mastitis (CM) produced by Gram-positive and Gram-negative bacteria (Lange-Consiglio et al. (2014)). The results obtained in that study were encouraging because the platelet lysate resulted in a reduction in SCC of about 67% in cows with acute CM and of about 53% in cows with chronic CM, in comparison to treatment with antibiotics alone (52.5% and 15.4%, respectively) or the combination of both PRP and antibiotics (90.6% and 66.7%, respectively). However, the rate of microbiological cure was not established. Furthermore, although the platelet lysate was obtained through a frozen-and-thawed procedure for PRP preparation with a final platelet concentration of $1 \times 10^6$ /μl, no investigation was made into the concentrations of WBC or growth factors in the platelet lysate composition (Lange-Consiglio et al. (2014)).

There are currently no published reports about the therapeutic use of PRP formulations for treating SCM caused by Gram-positive bacteria in cows, or data pertaining to the immunologic response of the mammary glands of cows with SCM to treatment with PRP formulations.

SUMMARY OF THE INVENTION

An object of the present invention is to provide an effective alternative to antibiotic treatment of SCM in cows that is not inferior and that results in an improved anti-inflammatory profile in the milk of treated cows.

Provided is a pure platelet-rich plasma (P-PRP) composition, comprising: live platelets and leukocytes, and a mixture of anticoagulants and activating substances (i.e.: calcium salts and/or thrombin in an amount effective for treating subclinical mastitis caused by Gram-positive bacteria in a bovine. In embodiments, the live platelets and leukocytes are present in a sample of whole blood obtained from a healthy bovine of the Blanco-Orejinegro breed.

Another object of the invention is a method of preparing the P-PRP composition. In embodiments, the manufacturing process comprises: extracting a sample of blood from a bovine; collecting the blood sample in a bag with an anticoagulant additive; and subjecting the mixture to a single centrifugation cycle. As a result of this novel process, the P-PRP composition of the invention has a therapeutically effective concentration of platelets and leukocytes for treating subclinical mastitis caused by Gram-positive bacteria in bovine. In certain embodiments, the process further comprises storing the P-PRP composition under refrigerated conditions for up to 96 hours. In still other embodiments, calcium gluconate may be added to the composition to induce platelet release and clot formation.

Another object of the invention is to provide a method of treating or preventing subclinical mastitis in a mammal comprising administering to the mammal a therapeutically effective amount of the P-PRP composition. In embodiments, the mammal is a bovine or sheep.

The P-PRP composition may be administered to the mammal prior to or after the onset of infection associated with SCM. In embodiments, the P-PRP composition may be administered as an injectable composition with a pharmaceutically acceptable carrier. In certain embodiments, the composition may be administered topically or by intra-mammary injection to the mammary organ of the mammal.

In certain embodiments, the method may further include continuing to administered additional therapeutically effective amounts of the P-PRP composition to the mammal throughout a treatment period, which treatment period may range from 24-96 hours with the therapeutically effective amount of the P-PRP composition being administered every 12 hours.

DETAILED DESCRIPTION OF THE INVENTION

Figure 1A:
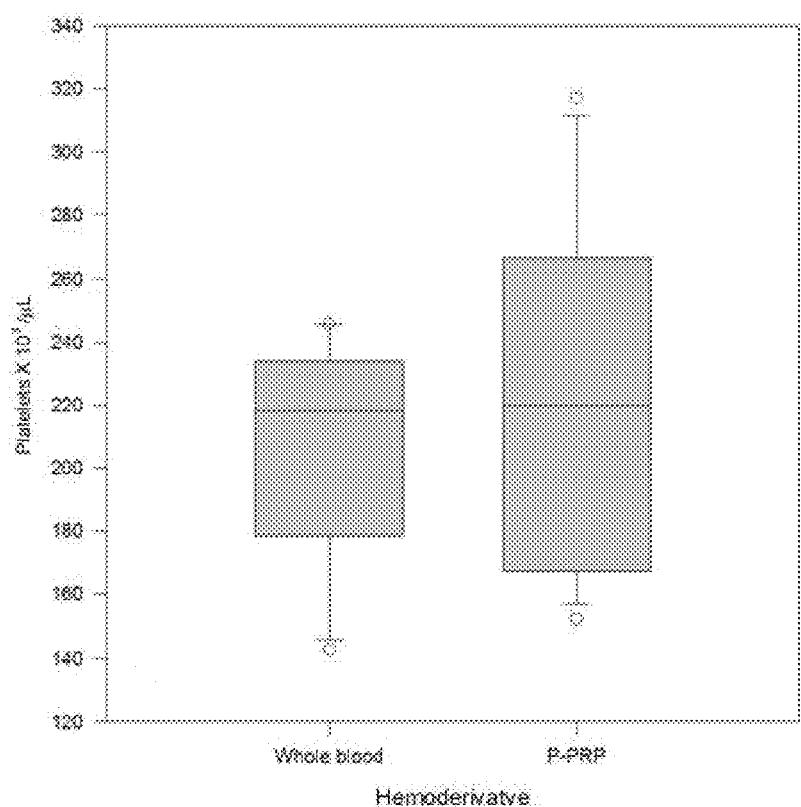
FIGS. 1A-1B show box plot representations of the median counts of platelets (FIG. 1A) and leukocytes (FIG. 1B) in hemoderivatives. P-PRP=pure platelet-rich plasma. *** =significantly different by U-Mann-Whitney test ($P<0.0001$).

The present invention may be understood more readily by reference to the following detailed description of the preferred embodiments of the invention. However, before the casting system, cast, different components and methods are disclosed and described, it is to be understood that this invention is not limited to specific cast types, assemblies or configurations, specific conditions, or specific methods, as such may vary and, and any modifications thereto and variations therein will be apparent to those skilled in the art. It is also to be understood that the terminology used herein is for the purpose of describing specific embodiments only and is not intended to be limiting.

Furthermore, the practice of the present invention will employ, unless otherwise indicated, conventionally known techniques in immunology, protein chemistry, biochemistry and molecular biology that are within the level of skill of persons skilled in the art.

A. Definitions and Abbreviations

It must be noted that as used herein and in the appended claims, the singular forms "a," "an," and "the," include plural forms unless the context clearly indicates otherwise. Thus, for example, reference to "a material" includes one or more of such different materials, and reference to "the method" includes reference to equivalent steps and methods known to those of ordinary skill in the art that could be modified or substituted for the methods described herein.

As used herein, "administering" refers to various means of introducing a target composition to a cell or tissue, or to a subject. These means are commonly known in the art, include those specifically discussed herein.

As used herein, "treating" means curing or ameliorating symptoms in a mammal associated with subclinical mastitis. As used herein, the terms "treat" or "treatment" refer to relief from, or alleviation of at least one symptom associated with SCM, or to slow or reverse the progression of SCM.

The terms "prophylaxis" or "preventing" as used herein mean preventing or avoiding the occurrence of an infection associated with subclinical mastitis, or tempering the severity of such infection if it is later contracted by a mammal.

As used herein, "therapeutically effective amount" means a dose sufficient to either prevent or treat subclinical mastitis in a mammal. Dosages of the P-PRP composition that can prevent or treat SCM in a mammal can be determined by persons skilled in the art in view of the disclosure, as a comparison of the appropriate treatment groups to the controls will indicate to those skilled in the art whether a particular dosage is effective in preventing or treating a disease used in a controlled challenge. In general, however, effective dosage will vary depending on the mode of administration as well as the state of the infection and the infected mammal.

"CM" refers to clinical mastitis.
"SCM" refers to subclinical mastitis.
"SCC" refers to somatic cell count.
"PC" refers to a platelet concentrate.
"PL" refers to a platelet lysate that does not contain live cells.
"PRP" refers to platelet-rich plasma.
"L-PRP" refers to leukocyte-platelet-rich plasma.
"P-PRP" refers to pure platelet-rich plasma.
"PRG" refers to a platelet-rich gel.
"WBC" refers to white blood cells or leukocytes.
"GF" refers to growth factors.

B. Pure Platelet-Rich Plasma (P-PRP) Composition

Pure platelet-rich plasma (P-PRP) is a substance typically considered to be a platelet concentrate (PC), either with or without a negligible concentration of leukocytes (WBC). When WBC counts are increased in a PC, the substance is generally referred to as leukocyte-platelet-rich plasma (L-PRP). In the field of regenerative medicine, PRP or PC implicate a substance with live platelets and WBCs, which in their fresh state are suitable for use in the treatment of various illnesses. When these substances comprising live platelets and live leukocytes (WBCs) are used, they produce a sustained and synchronic release of proteins, such as growth factors (GF), cytokines and chemokines from their cells' contents.

Other platelet-related substances exist that comprise non-live cells, such as platelet lysates (PL) or the plasma releasates from clots of PRP that was activated with calcium salts and/or thrombin. PLs may be obtained from a PC (either P-PRP or L-PRP) that has been exposed (frozen) to very low temperature episodes (−80° C.) and thawed during alternating thawing periods. Additionally, PLs may be obtained by inducing chemical and physical damage to cell membranes. For example, chemical damage to cells may be produced by non-ionic detergents that are toxic to tissues, and physical damage may be produced with an ultrasound.

Based on the foregoing distinctions between platelet-related substances, it is generally understood by persons skilled in the art that a PL cannot be considered to be a PC because PLs do not contain live cells. That is, PLs merely contain proteins derived as a result of cell lysis or damage. In this sense, the quality of the proteins from PL can be negatively affected or denatured. Similarly, although platelet releasates contain proteins derived from cell activation, they do not contain the cells themselves. Such proteins are therefore typically less negatively affected because they were obtained by using a more physiological procedure, i.e., obtained from PC incubated with activating substances at room temperature (37° C.) and then conserved frozen (−24° C.) for ulterior use.

The P-PRP composition of the invention was originally obtained from whole blood of heifers belonging to the Blanco-Orejinegro breed of cows in Colombia. Originally introduced to Colombia by Spanish conquerors in the XV century, the Blanco-Orejinegro breed has suffered through the process of natural selection, and thus it is believed that the P-PRP obtained from the blood of this breed may have a better immune profile than that from cows of other specialized diary breeds (e.g., Holstein and Swiss Brown cows).

In preferred embodiments, the P-PRP composition is obtained by the method further described herein and contains live cells in desired concentrations. The desired concentrations of live cells in the P-PRP composition preferably range from 160-1000×10$^3$ platelets/µL, 0.0-4×10$^3$ WBCs/µL and 0.1-4×10$^3$ WBCs/µL. For example, the P-PRP composition according to certain embodiments may contain 250-800×10$^3$ platelets/µL, and from 0.5-3×10$^3$ WBCs/µL or 1-2×10$^3$ WBCs/µL.

In embodiments, the composition further comprises an anticoagulant and/or a calcium salt, such as calcium gluconate.

Suitable anticoagulants for use in embodiments of the invention include those known in the art, such as, e.g., sodium citrate, acid citrate dextrose ("ACD") and citrate phosphate dextrose ("CPD"). Sodium citrate (the corresponding sodium-based salt of citric acid) is an advantageous anticoagulant as it provides good buffering capabilities over a range of pH. Anticoagulants used in embodiments of the invention will typically include solutions comprising citrate, phosphate, adenine, sodium chloride, and sugar or sugar alcohols. A citrate concentrate of at least 4 mM is desirable for anticoagulation in the original plasma; phosphate (usually of sodium) and adenine help maintain high levels of erythrocytic adenosine triphosphate ("ATP"), which is depleted during storage; and sugars, such as dextrose, provide for RBC metabolism. Both ACD and CPD solutions may be used, as well as CPDA-1 and CPDA-2, which also include adenine. In embodiments, the P-PRP composition may comprise the anticoagulant in a ratio of 0.5-2:10, such as 1.5:10, or about 1:7.

In certain embodiments, the P-PRP composition further comprises an activating substance that activates the platelets to release certain growth factors (cytokines) and induces clot formation. Specifically, the cell membranes of the platelets become "activated" by the activating substance to release contents of the alpha granules of the platelets. This release of agents is conventionally referred to as the "releasate" (i.e., the internal contents of the platelet, including growth factors). The P-PRP composition therefore further includes various proteins of the releasate (e.g., growth factors).

As a result of the addition of calcium salt, prior to administration as described in the production method below, the P-PRP composition comprises extracellular proteins selected from the group consisting of TGF-β1, PDGF-BB, PF-4, and C3. The P-PRP composition comprises TGF-β1 at least the following proteins in the respective concentration ranges: TGF-β1 present in a concentration of 5-200×10$^3$ pg/mL, PDGF-BB present in a concentration of 4-80×10$^3$ pg/mL, PF-4 present in a concentration of 6-20×10$^3$ pg/mL, and C3 present in a concentration of 40-80×10$^3$ pg/mL.

The activating substance used in the P-PRP composition may be selected from conventionally known substances for inducing release of platelet growth factors, such as (but not limited to) calcium gluconate, calcium chloride, thrombin, sodium gluconate, and combinations thereof. In preferred embodiments, the activating substance is a calcium salt solution, such as calcium gluconate or calcium chloride. The activating substance (e.g., calcium salt) may be present in the final P-PRP composition in a ratio ranging from 1:2 to 1:15 by weight of the composition, such as in a ratio of about 0.5-1.2:10 by weight of the composition. In certain embodiments, the P-PRP composition comprises calcium gluconate as the activating substance in a concentration of 8-10 mg/mL, such as 9.3 mg/mL.

Another aspect of the present invention is a pharmaceutical/veterinary product comprising the P-PRP composition described herein. Such pharmaceutical or veterinary product may include a platelet gel, platelet glue, growth factors-enriched fibrin glue and/or sealant, artificial scaffolds, and the like.

C. Production Method

PCs are conventionally obtained by three general procedures: (1) manual tube or bag protocols; (2) semi-automated kits; and (3) apheresis. Significant scientific information exists regarding protocols for obtaining PCs in man and animals. In a general sense, the relative centrifugation force (RCF) or "g" and the time of centrifugation will influence the final concentration of platelets and WBCs in a PC, and consequently the profile of proteins contained in the substance. Although it was formerly considered that a higher concentration of platelets (e.g., 1 million or more of platelets/µL of PC) would produce a better tissue response, there is currently enough data to reject this assumption, as an excess of growth factors and particularly pro-inflammatory cytokines could potentially be harmful for cells. Furthermore, it is also important to consider that when a higher quantity of platelets are concentrated by using either a tube or bag protocols or any semi-automated kit, this also implicates a great concentration of leukocytes in the final obtained PC, these leukocytes being primarily responsible for the production and release of higher concentrations of pro-inflammatory cytokines.

As briefly described above, embodiments of the invention are directed to a simple and efficient method for producing the P-PRP composition. The therapeutic P-PRP composition was produced by a novel method of PC procurement, including: (1) obtaining a sample of blood from a healthy bovine; (2) collecting the blood sample in bags containing an anti-coagulant or preservative additive; (3) subjecting the composition to a single centrifugation cycle; and (4) adding an activating substance to the composition. Optionally, the method described herein may also comprise a storage step, wherein the P-PRP composition may be stored (refrigerated at about 4° C.) for up to 96 hours. In embodiments where the composition is stored before use, addition of the aactivating substance (step (4)) occurs after such storage and shortly before use/administration of the P-PRP composition.

Figure 1B:
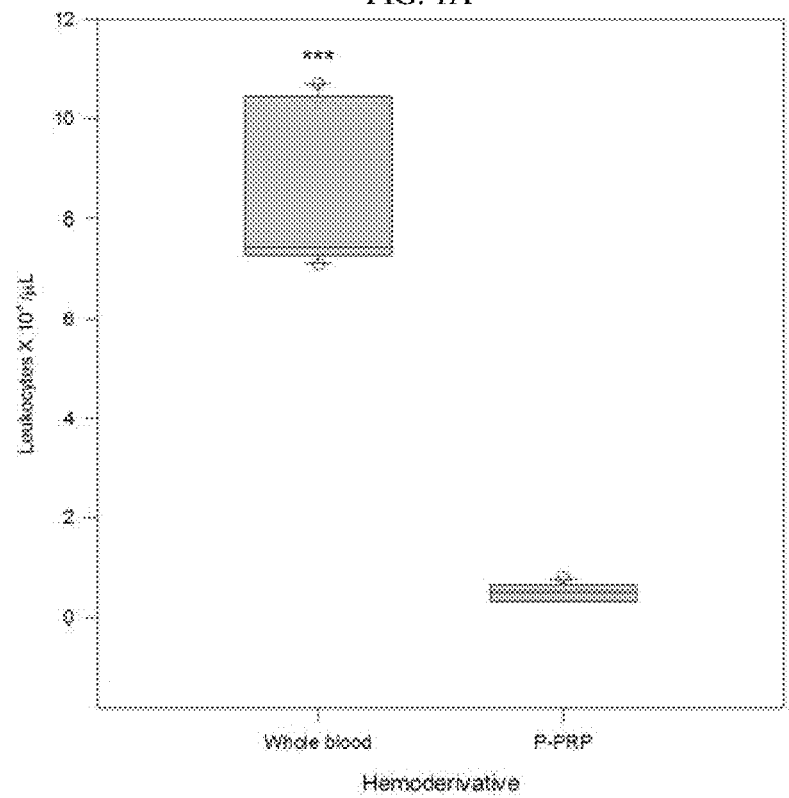

The obtaining of the blood sample may be by extraction with a 14-16 G needle coupled to the bag system. In embodiments, the blood sample is extracted from a healthy bovine using a needle and immediately collected in bags. Preferably, the blood sample is collected in 450-500 mL double blood bags containing an amount of an anticoagulant as described herein. The single centrifugation of the mixture includes centrifuging blood directly obtained from the bags or still in the bags at about 600-900×g for 1-12 minutes at 4-22° C. No further centrifugation step(s), dilution, or separation of the composition are necessary, as the process described herein results in the P-PRP composition having the desirable concentration of platelets and WBC (FIGS. 1A-1B). In the final step, prior to administration, an activating substance is added to the composition.

The anticoagulant added to the composition may be selected from known anticoagulants, and added in a ratio of 0.5-2:10. In certain embodiments, CPDA-1 (citrate, phosphate, dextrose and adenine) is added as the anticoagulant in a ratio 1:7.

The activating substance is added to the composition to affect the release of desired proteins as described above. Conventionally known activating substances or platelet release factors may be used. In certain preferred embodiments, calcium gluconate, or other calcium salts such as calcium chloride, are used as the activating substance and are added to the composition in a concentration of about 8-10 mg/mL or 9.3 mg/mL. In embodiments, the activating substance is added to the composition less than 15, 10, 5 or 1 minutes before administration, in a ratio of from 0.5:5 to 1:15, such as 1:10 or 1:12, to induce platelet release and clot formation. In certain embodiments, the activating substance is added to the composition about 30 seconds before administration.

D. Therapeutic Methods

The P-PRP composition described herein is suitable for use in the treatment and prevention (prophylaxis) of external and internal inflammatory states of mammals, preferably for the treatment of ailments of the mammary gland caused by bacterial infections of a bovine. In certain embodiments, the invention also relates to methods of treatment and prevention of SCM caused by Gram-positive bacteria in mammals, such as bovine or sheep or goat.

Typically, the P-PRP composition of the invention is administered by intramammary injection, but therapeutically effective dosages may also be administered by other means. That is, a further advantage is the versatility of use of the P-PRP composition of the invention, which may be injected by means of a syringe or applied externally (topically) in the form of a cream (gel). In preferred embodiment, the P-PRP composition is administered by topical application to the udder.

When administered as an intra-mammary injectable, the P-PRP composition may be administered using a pharmaceutically acceptable vehicle or excipient, such as (but not limited to) water, saline, dextrose, glycerol, ethanol, or the like, and combinations thereof. If desired, the vehicle may also contain auxiliary substances such as wetting or emulsifying agents or pH buffering agents.

Therapeutically effective dosages of the P-PRP composition may fall within a relative large range based on various factors that will be readily understood by persons skilled in the art. For example, if administered intra-mammarily, therapeutically effective dosages of the P-PRP composition will depend on the weight of the animal, and will typically range from 5 to 30 mL of the P-PRP per each udder quarter. Aside from the mode of administration, the therapeutically effective amount of the P-PRP composition to be administered to an animal will also depend on the number and timing of the dosages. For example, multiple administrations of the P-PRP may be given to an animal, typically at least about 12 hours apart, and at least twice or three times. In certain embodiments, it may be desirable to administer even more dosages to the animal, such as three, four, five, or even seven dosages.

Single dose administration will typically contain from about $5\text{-}200\times10^3$ pg/mL of TGF-$\beta$, $4\text{-}80\times10^3$ pg/mL of PDGF-BB, $6\text{-}20\times10^3$ pg/mL of PF-4 and $40\text{-}80\times10^3$ pg/mL of C3.

It will be understood by person skilled in the art in view of the present disclosure that the precise combination of dosage and timing with respect to administering a therapeutically effective amount of the P-PRP composition to an animal will be subject to significant variation.

In embodiments, the P-PRP composition may be administered to an animal prior to infection or SCM, thus serving as a prophylactic. Alternatively, the P-PRP composition may be administered to an animal having SCM or showing signs of infection.

An important advantage of the invention lies in the fact that administration of the P-PRP composition, as an alternative to conventional antibiotics treatments, does not require the milk produced by the bovine during treatment to be discarded, nor does treatment with the P-PRP composition result in a reduction in milk production.

E. Other Embodiments

Also provided are kits comprising a collection container, an anticoagulant, an activating substance, and instructions for a user to produce and/or administer the P-PRP composition on site to a mammal (e.g., bovine) in need thereof. The anticoagulant and the activating substance may be selected from those described herein. Kits of the invention may also comprise a blood sample that has already been drawn from a healthy cow. Such kits may contain the blood sample already mixed with a desirable amount of an anticoagulant as described herein, the mixture being provided in a stored condition (refrigerated at around 4° C.) and being suitable for use within 96 hours. Kits of the invention may additionally contain suitable instruments for preparation and use (administration) of the P-PRP composition.

F. Other Embodiments

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

A. Materials and Methods

A non-inferiority randomized clinical trial was conducted, following methodology described in Schukken et al., "Non-inferiority Trial Comparing a First-Generation Cephalosporin With a Third-Generation Cephalosporin in the Treatment of Nonsevere Clinical Mastitis in Dairy Cows," J. Dairy Sci. 96(10): 6763-74 (2013). The study was directed to determining whether treatment with the novel product (P-PRP activated with calcium gluconate) is [1] inferior to the reference product (cefquinome sulphate) as applied to the control group, and [2] not inferior by more than the predefined margin ($-\Delta$), namely:

$$H_0: [R_{cure}(\text{cefquinome}) - R_{cure}(\text{P-PRP})] \leq -\Delta \quad [1]$$

$$H_a: [R_{cure}(\text{cefquinome}) - R_{cure}(\text{P-PRP})] > -\Delta \quad [2]$$

where "$R_{cure}$" is the cure risk and "$\Delta$" is the non-inferiority margin. Results were interpreted according to the principles for a non-inferiority trial (Piaggio et al., "Reporting of Noninferiority and Equivalence Randomized Trials: Extension of the CONSORT 2010 Statement," JAMA 308(24): 2594-604 (2012); Schukken et al. (2013)). Thus, rejecting $H_0$ results in acceptance of $H_a$, indicating that the novel product (P-PRP) is not inferior to the reference product (cefquinome sulphate).

Sample size calculation was based on previous results using platelet concentrates for the treatment of CM, assuming that P-PRP cure risk was approximately 35% (Lange-Consiglio et al., "Intramammary Administration of Platelet Concentrate as an Unconventional Therapy in Bovine Mastitis: First Clinical Application," J. Dairy Sci. 97(10):6223-30, (2014)), and a significance level of 5% and power of 80% were selected. Selection of $\Delta$ is usually based on results of negative controlled trials, wherein $\Delta$ will be no more than half the effect expected from a superiority study (Piaggio et al., "Reporting of Noninferiority and Equivalence Randomized Trials: An Extension of the CONSORT Statement," JAMA 295(10): 1152-60 (2006)).

However, as no negative controlled studies of treatment of subclinical mastitis in cows using P-PRP appear to have been conducted to date, the $\Delta$ was chosen as half of the effect of the results reported by Lange-Consiglio et al. (2014). That is, should there be a true difference in favor of the experimental treatment of 5%, then 108 cows (i.e., 54 cows per group) with subclinical mastitis were determined to be required for 80% certainty that the upper limit of a one-sided 95% confidence interval (or equivalently a 90% two-sided confidence interval) will exclude a difference in favor of the reference group of more than 17.5%.

Dairy Herds and Animals

To be eligible for inclusion in the study, cows had to (a) be in parity 1 to 5, (b) not have blind mammary quarters, (c) not have experienced any cases of clinical mastitis in the current lactation, and (d) not have received treatment with antibiotics for any other disease in the last 30 days.

A total of 103 cows from nine commercial herds in Caldas and Risaralda, Colombia were selected for the study. The cows were managed under rotational grazing systems, and received supplementation with concentrates according to milk yield. Predominant pastures were a mix of Kikuyu grass (*Pennisetum clandestinum*), Orchardgrass (*Dactylis glomerata L.*), and Yorkshire fog grass (*Holcus lanatus*). Supplemented concentrates included mixes of cereals containing between 14% and 16% of crude protein and approximately 2.9 Mcal of metabolizable energy/kg of dry matter. The cows received the concentrates starting three weeks before calving (2 kg/cow/day), and continued at a rate of 1 kg per 4 kg of milk yield after calving. Mineral supplements and water were available ad-libitum.

Two individual composite milk samples were aseptically collected from each cow during the first visit to the herd in order to select the cows to be treated for subclinical mastitis. These milk samples were refrigerated and submitted to Universidad de Caldas for analysis, with one of the samples being used for analysis of subclinical mastitis using an automated cell counter (FOSSOMATIC, from Foss, Hillerd, Denmark). The subclinical mastitis results were expressed as the natural log (LnSCC), in thousands/mL to normalize the data distribution. Based on results of the analysis for subclinical mastitis, the second sample was used for bacteriological and molecular analyses whenever SCC was $\geq$100,000 cells/mL in primiparous, and $\geq$200,000 cells/mL in multiparous, cows (Schepers et al., "Estimation of Variance Components for Somatic Cell Counts to Determine Thresholds for Uninfected Quarters," J. Dairy Sci. 80(8): 1833-40 (1997)).

Microbiological analyses were performed according to protocols established by the National Mastitis Council (Adkinson et al., "Implications of proposed changes in bulk tank somatic cell count regulations" J Dairy Sci. 84(2):370-4 (2001)).

The milk samples were streaked onto agar plates containing 5% sheep blood and 0.1% esculin. The agar plates were incubated at 37.5° C. and visually inspected at 24 hours and 48 hours for bacterial growth. Morphology and Gram staining were used for initial identification. A catalase test was used to differentiate *staphylococci* from *streptococci*, and a coagulase test was performed on catalase-positive cocci to confirm presence of *Staphylococcus aureus*. Gram-positive and catalase-negative cocci were differentiated by their reaction to the hydrolysis of esculin under ultraviolet light. The Christie, Atkins, Munch-Petersen (CAMP) test and esculin reaction were used to differentiate *Streptococcus agalactiae* and *Streptococcus dysgalactiae*, and esculin reaction and culture in enterococcosel agar (from Becton-Dickinson, Durham, N.C., USA) were used to identify *Streptococcus uberis*. Their morphology and Gram staining were used to identify *Corynebacterium* species. Growth in McConckey agar and further biochemical tests, such as citrate, indole, oxidase and motility, were used to identify coliforms. Those cultures that presented more than two bacterial species were considered contaminated and not informative of intramammary infection.

The intramammary infection was declared when a composite milk sample presented a SCC higher than the established cut points, and the microbiologic culture was positive for any Gram-positive mammary pathogens. All culture-positive cows (i.e., positive for major Gram-positive pathogens) meeting the selection criteria were selected for treatment.

Treatment Protocols

Cows with subclinical mastitis were randomly allocated to one of two treatments as follows:
- 54 total diagnosed cows were treated with P-PRP to constitute the "Experimental Group" (EG); and
- 49 total diagnosed cows were treated with cefquinome to constitute the "Reference Group" (RG).

The initial treatment was administered 4 days after the first milk sampling. Cows of both groups (EG) and (RG) were treated after milking for three consecutive makings with either:

(1) an intramammary infusion of 10 mL P-PRP activated with calcium gluconate (9.3 mg/mL) (Ropsohn Therapeutics, Bogota DC, Colombia) in a proportion of 1:10; or (2) an intramammary infusion of 75 mg of cefquinome sulphate (COBACTAN L.C. from Merck Animal Health, Madison, N.J., USA)

Blood Samples for P-PRP Preparation

The P-PRP was obtained from four Blanco Orejinegro heifers, ranging between 12-18 months of age and having a mean body weight of 300±20 kg. The heifers were sedated with xylazine (0.01 mg/kg, IM) and restrained in right lateral recumbence on a surgical table. The skin of the left lateral jugular vein was first aseptically prepared for blood extraction using an iodine povidone scrub and cleared with ethyl alcohol, and a small area of the skin over the jugular vein in the central region of the neck was desensitized by injecting 2 mL of lidocaine (2%). Then, a sterile surgical blade was used to make a 3 mm skin incision, a 14 G catheter was put into the jugular vein, and a heparin rubber cap was put on the free extreme of the catheter to avoid the risk of bleeding. The blood was obtained from each donor heifer by coupling the needle of a double transfusion bag to the rubber cap. As the blood was extracted into the transfusion bag, the bag was under constant and smooth agitation/shaking so as to mix the blood with the anticoagulant. During each round of blood extraction, three bags (500 mL each) were obtained from each heifer. Normally, blood extraction was carried out from the selected heifers every 10 days until the completion of treatments. All heifers were closely monitored for anemia and any other health issue.

Cellular and Molecular Quality Control of P-PRP

Blood bags were centrifuged in a stationary centrifuge (RotoSilenta 630 RS from Hettich, Tuttlingen, Germany) at 1600 g for 8 minutes. Then, the plasma fraction (P-PRP), including the buffy coat, was transferred to the plasma bag that was separated from the blood bag. The P-PRP was gently homogenized, and packed in 10 mL syringes in a laminar flow cabinet. The free extreme of each P-PRP syringe was protected with a plastic sterile cap. An additional sterile reaction tube containing 1 mL of calcium gluconate was packed with the 10 mL syringe containing the P-PRP in a plastic bag. The calcium gluconate was added to the P-PRP right before the intramammary infusion.

Thirty P-PRP syringes of 10 mL each were randomly chosen to carry out a blood count using automated equipment (Celltaca MEK-6450 from Nihon Kohden, Tokyo, Japan). Samples were also analyzed for the concentration of protein releasates in P-PRP (i.e., transforming growth factor beta 1, TGF-$\beta$1; platelet-derived growth factor BB, PDGF-BB; platelet factor 4, PF4; and plasma complement component 3, C3) by ELISA. The P-PRP was incubated for 6 hours with calcium gluconate in a dilution of 10:1. The same molecules were measured in blood plasma (i.e., a negative control) obtained using the same anticoagulant but centrifuged at a higher speed (5000 g). As a positive control, P-PRP samples incubated with a 0.5% of a solution of a non-ionic detergent (TRITONX100 from PanReacAppliChem, Barcelona, Spain) (platelet lysates) in dilution 10:1 for 15 minutes were used.

Sampling Procedure and Laboratory Analyses

Once cows were treated, composite milk samples from both treated groups were collected at days 21 and 22 after treatment for SCC and microbiological analyses. Procedures for SCC and microbiology were previously described. Treatment was repeated in cows that remained positive for major Gram-positive bacteria, receiving the same product used for the first treatment 4 days after collecting the second milk sample. A final milk sampling was conducted on all refractory cases 21 and 22 days after the repeated treatment. Individual cow SCC, including laboratory data and pre- and post-treatment concentration of cytokines (IL-1, IL-2, IL-4, IL-6, IL-8, IFN-$\gamma$, and TNF-$\alpha$), were generated for each milk sample. No more than two treatment attempts per cow were performed and used in the study.

Concentration of Cytokines in Hemoderivatives and Milk

Proteins were analyzed in hemoderivatives and whole milk using commercial ELISA development kits from R&D Systems (Minneapolis, Minn., USA) with the exception of IL-1, IL-4, IL-8 and C3. PDGF-BB (Human PDGF-BB DuoSet, DY220), TGF-$\beta$1 (Human TGF-$\beta$1 DuoSet, DY240E), and PF4 (Human CXCL4/PF4 Duoset, DY795), which were determined using human antibodies. Notably, TGF-$\beta$1 shares a high homology between these proteins in humans and cattle (Gibson et al., 1995). Furthermore, human PDGF-BB antibody has been used to also measure the same bovine protein (Dardik et al., "Shear Stress-Stimulated Endothelial Cells Induce Smooth Muscle Cell Chemotaxis Via Platelet-Derived Growth Factor-BB and Interleukin-1 Alpha," J. Vasc. Surg. 41(2): 321-31 (2005)), and PF4 presents a high homology between humans and ruminants (Shigeta et al., "Ovine Platelet Factor 4: Purification, Amino Acid Sequence, Radioimmunoassay and Comparison With Platelet Factor 4 of Other Species," Thromb. Res. 64(4): 509-20 (1991)).

Interleukin 1 (IL-1beta, ELISA Reagent Kit, Bovine, Thermo Fisher Scientific Inc., Waltham, Mass., USA), IL-2 (Bovine IL-2, Duoset ELISA, R&D Systems, Minneapolis, Minn., USA), IL-4 (IL-4 ELISA Development Kit, Mabtech AB, Nacka Strand, Sweden), IL-6 (Bovine IL-6, Duoset ELISA, R&D Systems, Minneapolis, Minn., USA), IL-8 (IL-8ELISA Development Kit, Mabtech AB, Nacka Strand, Sweden), IFN-$\gamma$ (Bovine IFN-gamma, Duoset ELISA, R&D Systems, Minneapolis, Minn., USA), TNF-$\alpha$ (Bovine TNF-alpha Duoset ELISA, R&D Systems, Minneapolis, Minn., USA), and C3 (Bovine Complement Component 3, ELISA Kit MyBioSourceInc., San Diego, Calif., USA) were assayed with bovine-specific antibodies. The standards provided for each ELISA kit were used in preparing each standard curve according to the manufacturers' instructions. Readings were performed at 450 nm. In general, the inter- and intra-assay coefficients of variation for the various ELISA kits were between 2-5%.

Primary and Secondary Outcomes

Cure was defined at the cow level. Specifically, cure was established in a cow that was infected at the beginning of the study and where the organism present was not isolated in the subsequent two post-treatment samples. Cure risk was statistically assessed for initial treatment (samples taken at days 21 and 22) and treatment of refractory cases samples (samples taken at days 47 and 48), independently. A single milk sample taken after treatment was used to determine both treatment and post-treatment cure risks. A reduction in the SCC was defined as a decrease in SCC for the two post-treatment samples compared to the first value at the start of the study. Changes in the concentration of milk cytokines were also used as criteria for cure and evaluation of the inflammation of the mammary gland.

Statistical Analysis

Platelet and leukocyte counts in whole and P-PRP were compared with a U-Mann-Whitney Test. To evaluate the quality of the P-PRP, the concentration comparisons of TGF-β1, PDGF-BB, PF-4, and C3 in hemoderivatives (plasma, platelet lysates and P-PRG releasates) were analyzed by one-way ANOVA, and if necessary, followed by a Tukey test.

The statistical analysis of the different outcomes was done using linear and logistic regression models according to the response variable (Dohoo et al. (2009)). The main predictor was the treatment group (EG and RG). The analyses took into account covariates such as herd, the parity of the cow, and LnSCC before treatment. The logistic regression model that was used for bacteriological cure was:

$$\text{Logit } (p \text{ of cure=1)=intercept+treatment+herd+parity+LnSCC} \quad [3]$$

where "cure" is bacteriological cure for major Gram-positive pathogens, "treatment" is a binary variable indicating either P-PRP (EG) or cefquinome sulphate (RG), "herd" is a set of indicator variables for dairy herd, "parity" is parity of the enrolled cow, and "LnSCC" corresponds to the natural log of the SCC value before treatment.

The statistical analyses of LnSCC and the milk concentration of IL-1, IL-2, IL-4, IL-6, IL-8, IFN-γ, and TNF-αresults were done using linear regression. The main predictor was treatment, and the fixed effects of covariates such as herd, parity, and LnSCC before treatment were also taken into account. The linear regression model used was:

$$y = \text{intercept+treatment+herd+parity+LnSCC+error} \quad [4]$$

where y corresponds to LnSCC after treatment on days 21 and 47 for cows treated one or two times, respectively, and the milk concentrations of IL-1, IL-2, IL-4, IL-6, IL-8, IFN-γ, and TNF-α, which were measured only at days 0 and 21. The other predictors were previously described.

The analyses were carried out in Stata 14.1 using the commands 'logit' and 'reg' (Stata Corp. College Station, Tex., USA). A P-value of <0.05 was accepted as statistically significant for all tests.

B. Cellular and Molecular Analysis of Proteins in P-PRP

The therapeutic composition of the invention was produced by the novel protocol of PC procurement described herein. This resulted in a particular concentration of platelets and WBCs in the therapeutic composition (P-PRP) that was further evaluated with respect to subclinical mastitis produced by Gram-positive bacterial. FIGS. 1A-1B show box plot representations of the median count of platelets (FIG. 1A) and leukocytes (FIG. 1B) in hemoderivatives. As shown in FIG. 1A, platelet counts were not statistically different between whole blood and P-PRP. However, leukocyte counts were significantly (P<0.01) lower in P-PRP as compared to the whole blood (FIG. 1B). Namely, the concentration of platelets obtained in P-PRP was similar to the concentration in whole blood, but WBC count in P-PRP was negligible when compared to whole blood.

Additional studies were performed to determine concentrations of various proteins involved in the therapeutic effect of the P-PRP composition. Specifically, TGF-β1 and platelet derived growth factor isoform BB (PDGF-BB) are some of the main growth factors contained in platelets, with TGF-β1 also being released by WBCs. Notably, both proteins have a powerful anti-inflammatory effect and PDGF-BB serves as a potent chemotactic agent for stem cells. The concentrations of these specific proteins were therefore measured (using ELSA technique), as well the concentrations of proteins having an antibacterial effect: one derived from platelets, platelet factor 4 (PF4); and the other contained in plasma, plasma complement fraction 3 (C3). The concentrations of these proteins are depicted in FIGS. 2A-2D.

To measure the concentrations, calcium gluconate solution (9.3 mg/mL) was added to the P-PRP composition in a ratio of 1:10. Calcium gluconate acts as an activating substance to induce platelet release and clot formation. The concentrations of the proteins in the plasma releasates from the clot-containing platelets (platelet-rich gel, PRG) were measured six hours after mixing the composition with the calcium gluconate solution. Concentrations of the aforementioned proteins were likewise measured in plasma (free of cells) from the same cows and in PLs obtained by mixing with a non-ionic detergent. The first substance (plasma) thus acted as a negative control for protein enrichment and PL acted as a positive control, because the non-ionic detergent produced 100% protein release by direct damage of cell membranes.

Figure 2A:
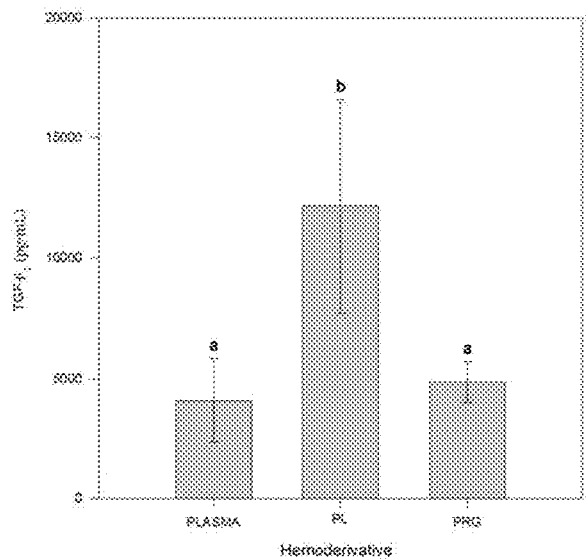
FIGS. 2A-2D show the mean 95% confidence intervals of the concentrations (pg/mL) of TGF-$\beta$1 (FIG. 2A), PDGF-BB (FIG. 2B), PF4 (FIG. 2C), and C3 (FIG. 2D) in hemoderivatives. Different letters represent significant differences at $P<0.05$ for each independent protein between hemoderivatives. PRG=Pure platelet-rich gel releasate; PL=platelet lysate.
Figure 2B:
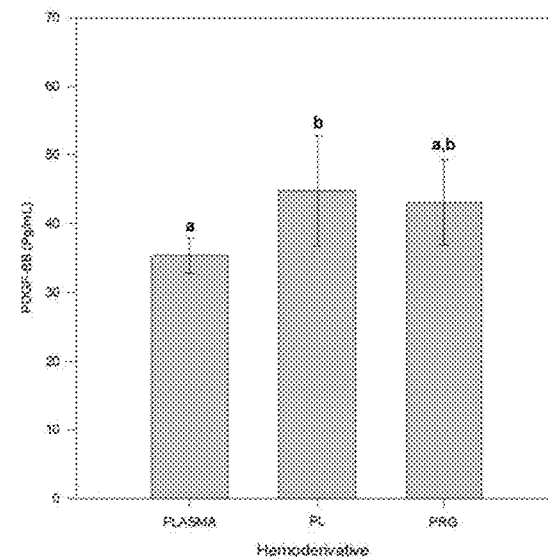
Figure 2C:
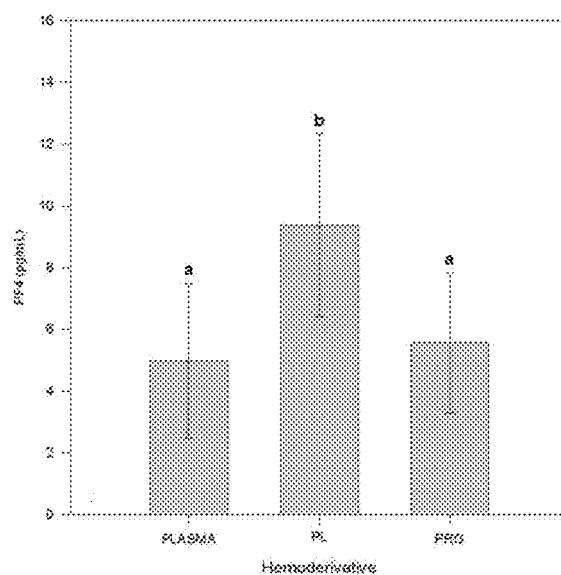
Figure 2D:
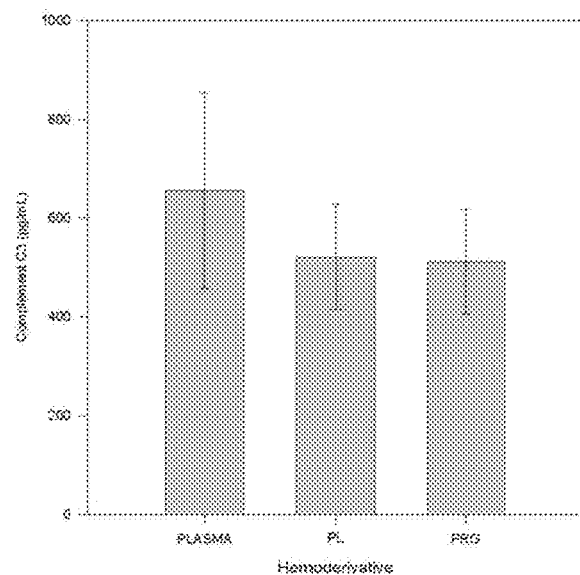

As shown in FIGS. 2A-2D, concentrations of TGF-β1 (FIG. 2A) and PF4 (FIG. 2C) were significantly (P<0.01) higher in PLs (positive control) as compared to PRG releasates and plasma. PDGF-BB concentration was also significantly higher in PL as compared to plasma, but not statistically different between plasma and PRG releasates (FIG. 2B). On the other hand, C3 concentrations were similar between the hemoderivatives (FIG. 2D).

C. Stability of Proteins in PRG Releasates and Their Kinetics of Release from P-PRP Clots Further evaluation was conducted to determine concentrations of the aforementioned proteins in PRG releasates over time (96 hours). The period of 96 hours was selected because the study of cows with subclinical mastitis included the use of an activated 10 mL P-PRP intramammary dose at 3 consecutive times every 12 hours (i.e., a 36 hour period). The results are presented in FIGS. 3A-3D, where the time of 0 represents the positive control (platelet lysate). That is, point 0 should be considered as the 100% release from the positive controls (PL).

Figures 3A, 3B:
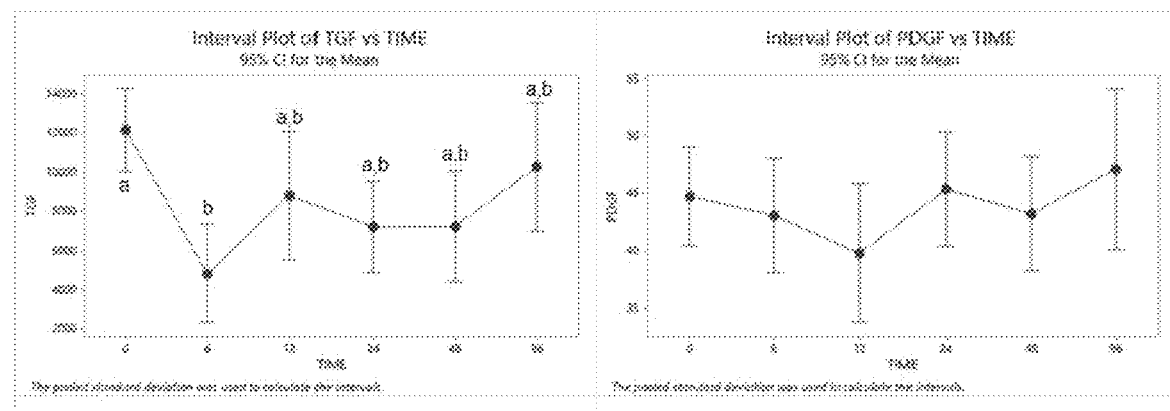
FIGS. 3A-3D illustrate the mean and 95% confidence intervals of the concentrations (pg/mL) of TGF-$\beta$1 (FIG. 3A), PDGF-BB (FIG. 3B), PF4 (FIG. 3C), and C3 (FIG. 3D) over a 96 hour period. Time "0" represents the positive control (platelet lysate) at the start of treatment. The different letters a-b represent significant differences ($P<0.05$) between the concentrations of proteins over time.
Figures 3C, 3D:
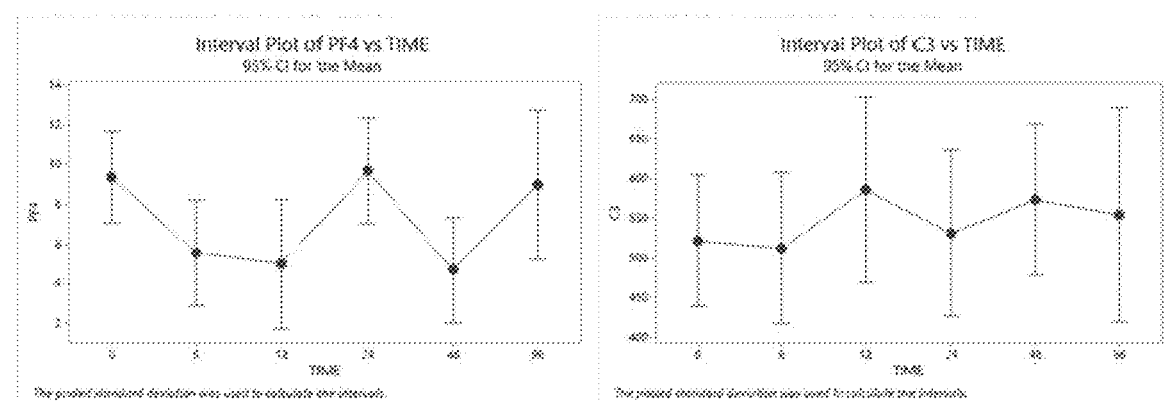

TGF-β1 was scarcely released (50% less) from PRG supernatants after 6 hours when compared with PLs, and there was a significant difference in the concentrations of this protein between PLs and PRG supernatants at the same time point. However, as shown in FIG. 3A, TGF-β1 was released in a similar concentration as PLs at the ulterior time points. PDGF-BB was released over time in a similar and massive pattern release as the same protein contained in PLs. Notably, as shown in FIG. 3B, PDG-BB was stable over time. PF4 showed a similar initial pattern release as TGF-β1. As shown in FIG. 3C, it was slowly released during the first 12 hours, then presented a peak in concentration at 24 hours, diminished at 48 hours, and finally again peaked in concentration at 96 hours. As shown in FIG. 3D, C3 was present in similar concentrations in PL and PRG supernatants at any point. Notably, the protein C3 was not denatured over 96 hours.

D. Intramammary Infections and Bacteriological Cure

The relative distribution of intramammary infections among the 103 cows tested before the start of treatment (time=0) at the time of subclinical mastitis detection is shown in Table 1 below.

TABLE 1

| Pathogen | Group | | Total |
| --- | --- | --- | --- |
| | EG | RG | |
| Staphylococcus aureus | 26 | 27 | 53 |
| Streptococcus uberis | 20 | 18 | 38 |
| Streptococcus agalactiae | 6 | 4 | 10 |
| Streptococcus dysgalactiae | 2 | 0 | 2 |

Figure 4:
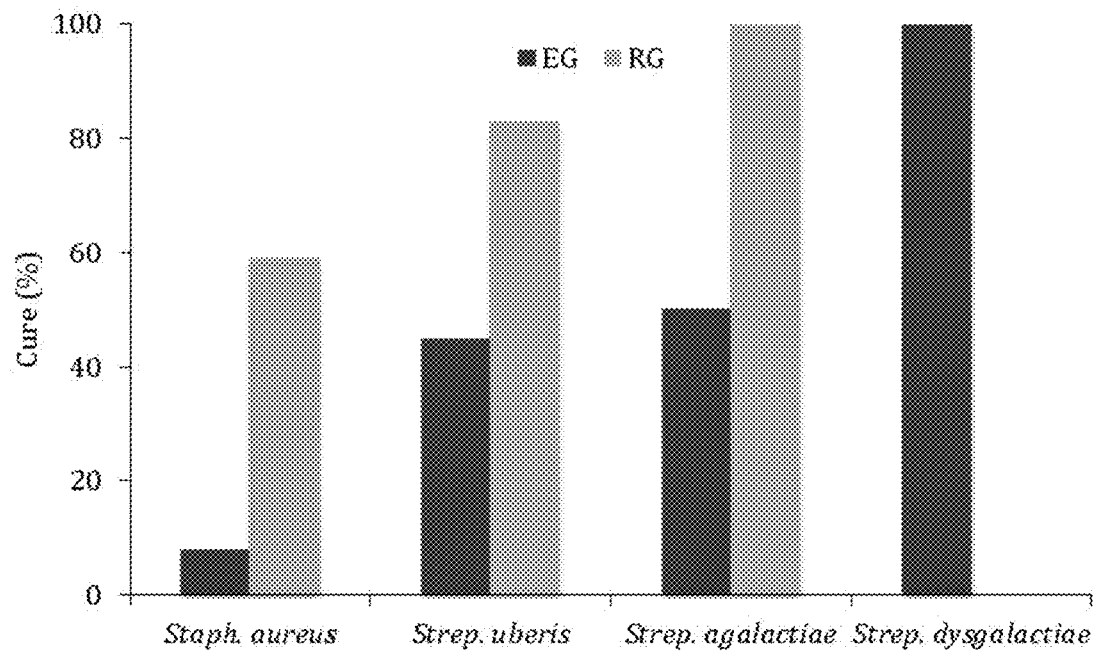
FIG. 4 provides graphs of the overall bacteriological cure for cows with intramammary infections caused by Gram-positive major pathogens and treated with P-PRP (EG) or cefquinome sulphate (RG). EG treatment is represent in dark greyscales and RG treatment is represented in light greyscales.
Figure 5:
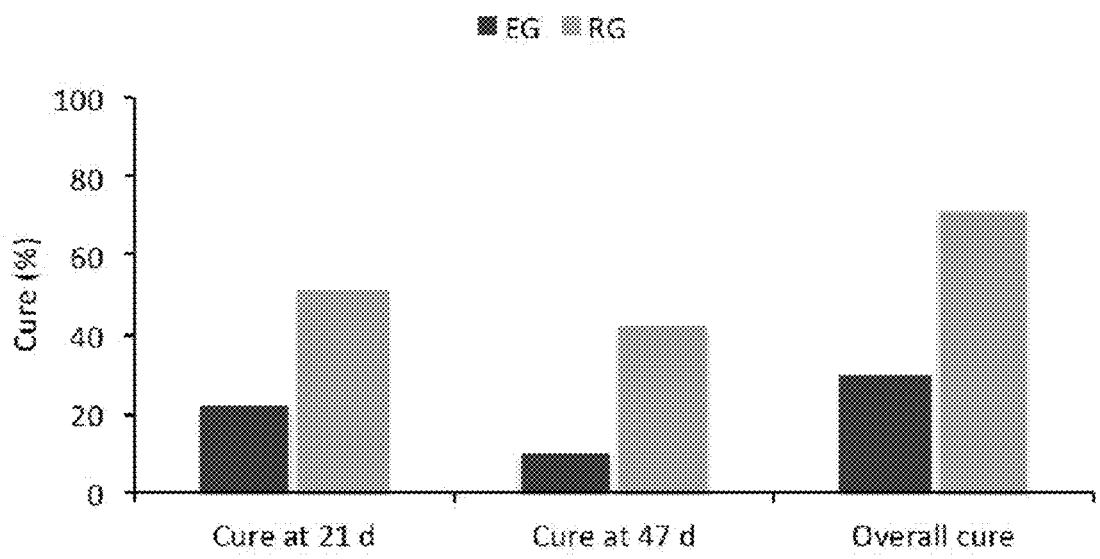
FIG. 5 provides graphs of bacteriological cure at days 21 and 47, as well as overall cure, in cows with intramammary infections caused by Gram-positive major pathogens after a second treatment with P-PRP (EG) or cefquinome sulphate (RG). EG treatment is represent in dark greyscales and RG treatment is represented in light greyscales.

Overall, bacteriological cure was observed in 16 cows (30%, n=54) of the EG, and in 35 cows (71%, n=49) of the RG. FIG. 4 shows the distribution of the bacteriological cure by initial bacteriological status (Gram-positive pathogens) and after treatment with P-PRP (EG) or cefquinomesulphate (RG). Some cows received two treatments because they were refractory to the first treatment. For these cows, FIG. 5 shows the bacteriological cure at days 21 and 47, as well as the overall cure by initial bacteriological status (Gram-positive pathogens) and by additional treatment with P-PRP (EG) or cefquinome sulphate (RG).

Logistic regression models of bacteriological cure demonstrated better cure risks in cows treated with cefquinome sulphate (RG) as compared to the cows treated with P-PRP. Table 2 below shows coefficients and standard error (SE) of the logistic regression model performed to evaluate the effect of treatment (with P-PRP or cefquinome sulphate) on the probability of bacteriological cure in cows with intramammary infections caused by Gram-positive major pathogens.

TABLE 2

| Effect | Coeff. | SE | P-value |
| --- | --- | --- | --- |
| Treatment: | | | <0.001 |
| P-PRP (EG) | 3.18 | 0.70 | |
| Cefquinome sulphate (RG) | Reference | | |
| Herd (1 to 9) | Not shown | | 0.007 |
| LnSCC | 0.31 | 0.20 | 0.11 |

The multivariable model showed a non-significant effect of parity (P=0.50), while the effect of LnSCC on the probability of cure at the start of treatment was slightly significant (P=0.08). Therefore, a second model that removed the variable parity was analyzed. This second model demonstrated an increase of the P-value for the effect of LnSCC at the beginning of the treatment trial (P=0.11). The effect of the herd was significant in both the full (P=0.015) and reduced (P=0.007) models, but the coefficients were not shown.

The cure risk for Strep. agalactiae could not be calculated with a logistic model because the cure risk in the RG was 100%. Additionally, there were only two cows infected with Strep. dysgalactiae, and both were treated with P-PRP and cured within 21 days after the start of treatment. Thus, the coefficients of the logistic model shown in Table 3 below are for the effects of treatment on the cur risk for only Staph. aureus and Strep. uberis.

TABLE 3

| Effect | Coeff. | SE | P-value |
| --- | --- | --- | --- |
| Treatment for Staph. aureus | | | 0.001 |
| P-PRP (EG) | −2.86 | 0.83 | |
| Cefquinome sulphate (RG) | Reference | | |
| Treatment for Strep. uberis | | | 0.02 |
| P-PRP (EG) | −1.81 | 0.78 | |
| Cefquinome sulphate (RG) | Reference | | |

Figure 6:
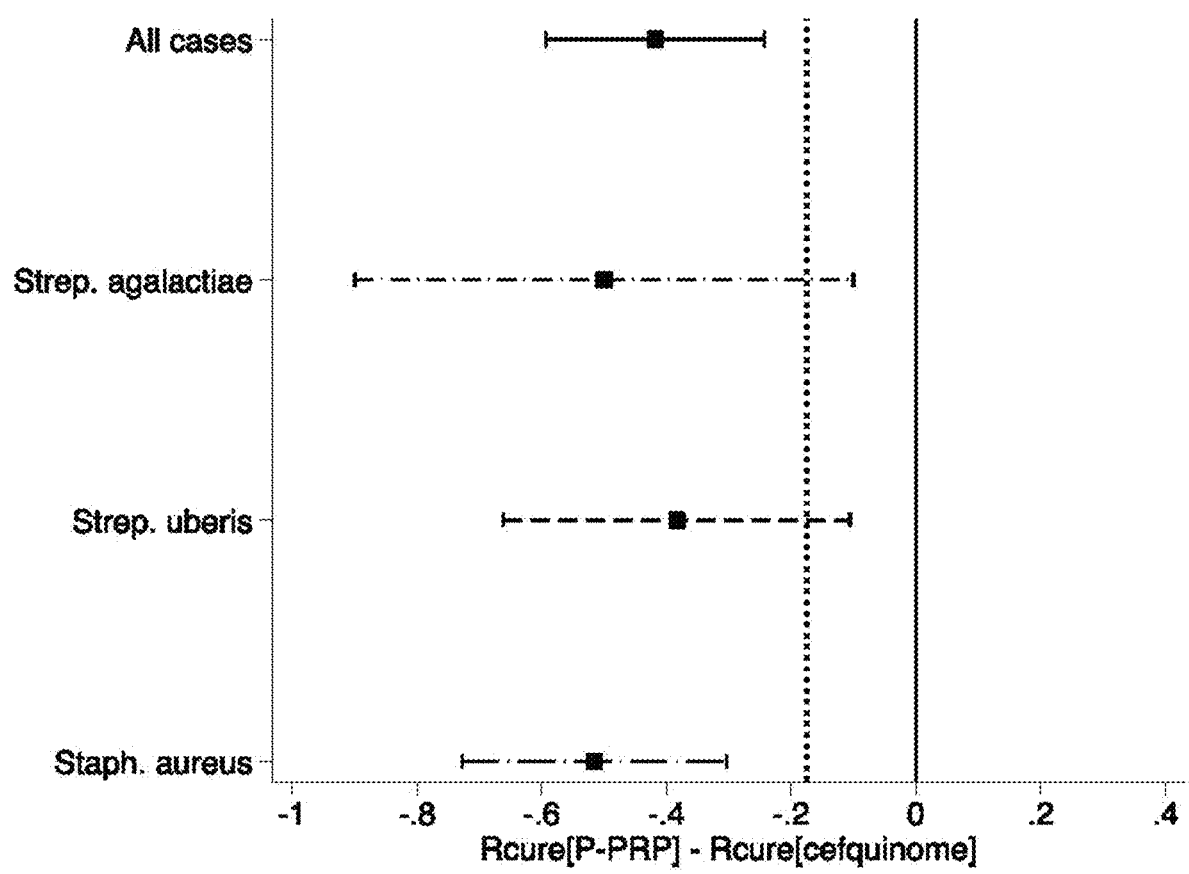
FIG. 6 is a graphical representation of the risk difference for bacteriological cure between both treatments (EG vs. RG). The black dotted vertical line represents the non-inferiority margin ($\Delta$), and the area to the right of this value (−0.175) is the zone of non-inferiority. The solid squares on the horizontal lines are the point-estimates of the difference in cure between P-PRP and cefquinome sulphate, and caps of the horizontal lines indicate 95% CI.

The above results show that the probability of bacteriological cure for infections caused by Staph. aureus was 0.06 times that of cefquinome sulphate (RG). In the case of infections caused by Strep. uberis, the probability of bacteriological cure was 0.16 times that of cefquinome sulphate (RG). The cure risk for each treatment was then used to calculate the risk difference [$R_{cure}$(P-PRP)=$R_{cure}$(cefquinome)]. Differences in bacteriological cure between both treatments (EG and RG) are shown in FIG. 6, which is a graphical representation of the risk difference for bacteriological cure between the treatments. Specifically, the dotted vertical line in FIG. 6 represents the non-inferiority margin ($\Delta$), with the area to the right of this value (−0.175) indicating the zone of non-inferiority. The solid squares on the horizontal lines are the point-estimates of the difference in cure between treatments with P-PRP and cefquinome sulphate, and the caps on the lines indicate 95% CI. With respect to the bacteriological cure of all cases, the CI does not span both zero and the non-inferiority margin (−$\Delta$), indicating that cefquinome sulphate treatment was better. With respect to the bacteriological cure in Strep. agalactiae cases, the CI spans −$\Delta$ but not, indicating that treatment with cefquinome sulphate is better, although non-inferiority is inconclusive. For the bacteriological cure of Strep. uberis, the CI also does not span both −$\Delta$ and zero, indicating that treatment with cefquinome sulphate is better.

E. Somatic Cell Count

Figure 7:
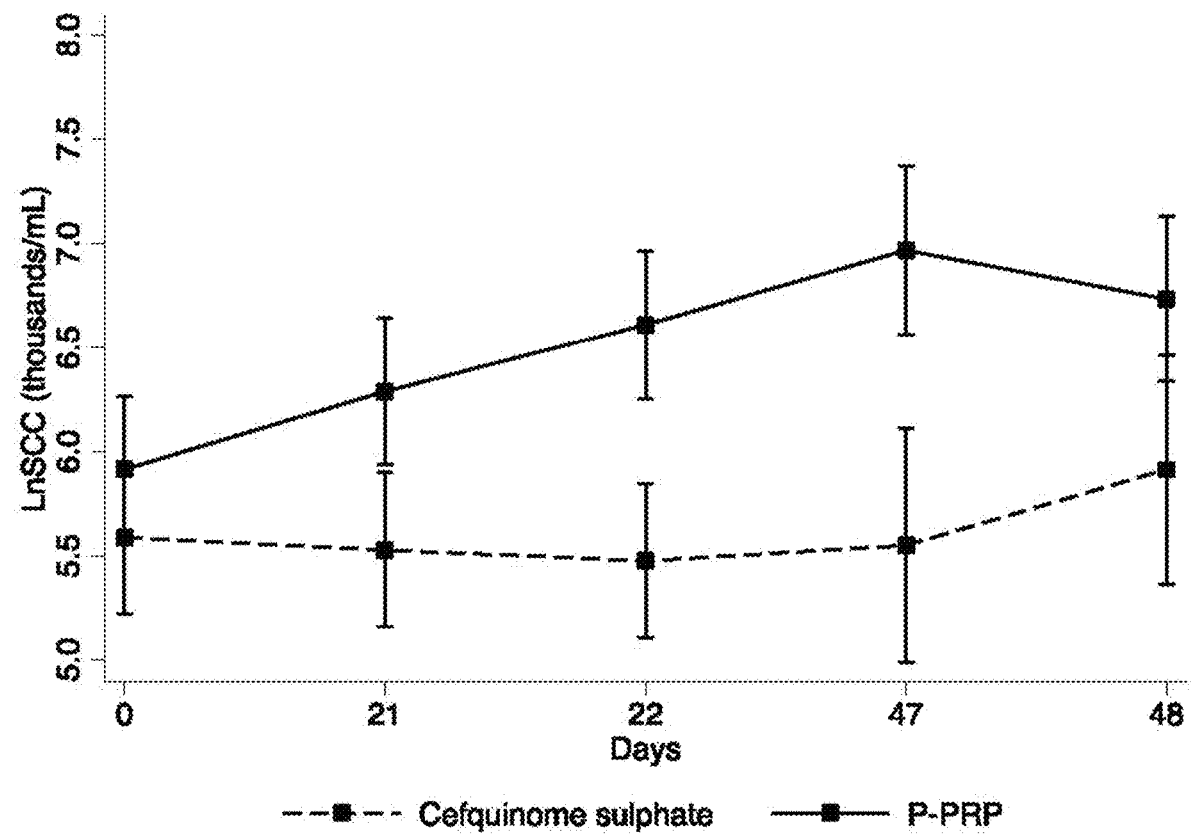
FIG. 7 shows the mean and confidence interval of LnSCC (thousands/mL) in cows with subclinical mastitis and treated with cefquinome sulphate or P-PRP. Zero represents the day of the treatment. The LnSCC on days 47 and 48 corresponds to cows treated twice, as they were refractory to the first treatment.

A total of 425 milk samples were collected from cows selected for treatment between day 0 (onset of treatment) and days 21, 22, 47 and 48, and analyzed for SCC. At the start of treatment, there were no differences for the LnSCC, and the geometric means for the P-PRP group (EG) and the cefquinome sulphate group (RG) were 370,000 cells/mL and 266,700 cells/mL, respectively. As shown in FIG. 7, the mean LnSCC significantly increased in the EG after the start of the trial, whereas no differences were observed in the mean LnSCC of the RG. The LnSCC of days 47 and 48 corresponds to cows that were treated twice because they were refractory to the first treatment.

F. Cytokine Concentrations in Milk

Figure 8A:
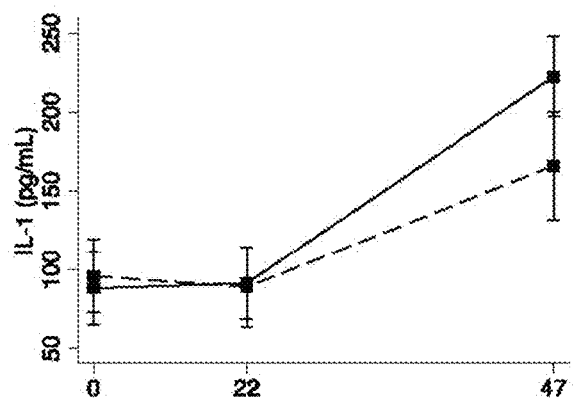
FIGS. 8A-8D show the mean concentration (95% CI) of IL-1 (FIG. 8A), IL-2 (FIG. 8B), IL-4 (FIG. 8C) and IL-6 (FIG. 8D) in the milk of cows with intramammary infections that were treated with cefquinome sulphate or P-PRP. Zero represents the day of the treatment, and day 47 corresponds to cows treated twice, as they were refractory to the first treatment.
Figure 8B:
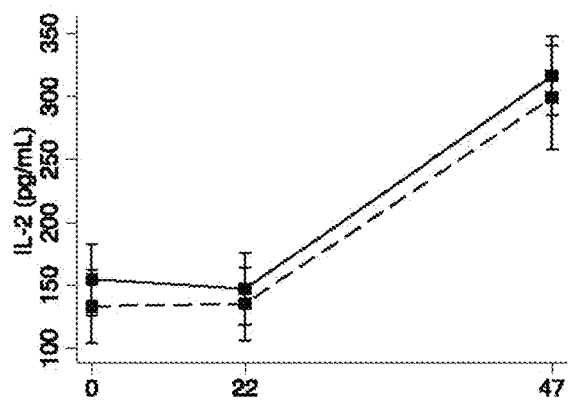
Figure 8C:
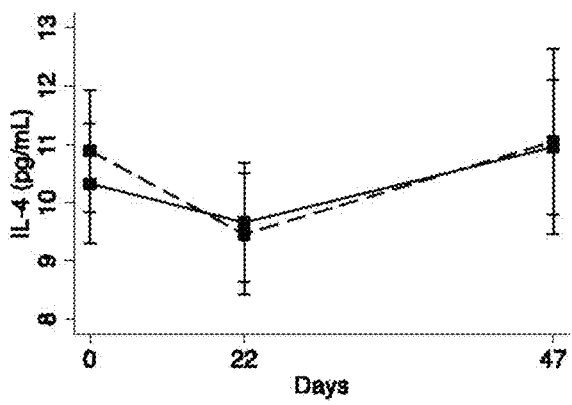
Figure 8D:
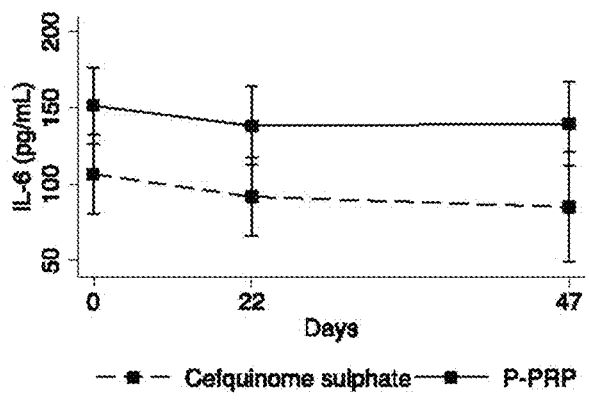
Figure 9A:
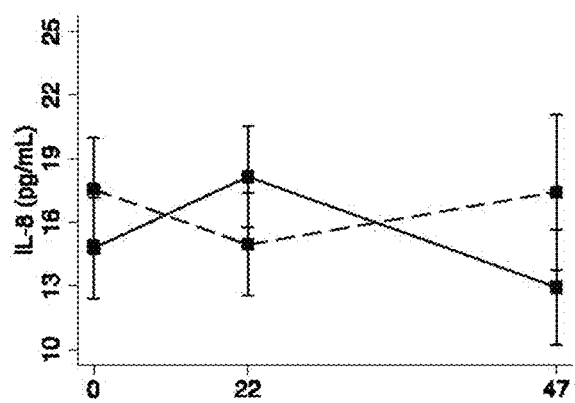
FIGS. 9A-9C show the mean concentrations (95% CI) of IL-8 (FIG. 9A), IFN-$\gamma$ (FIG. 9B), and TNF-$\alpha$ (FIG. 9C) in milk of cows with intramammary infections that were treated with cefquinome sulphate or P-PRP. Zero represents the day of the treatment, and day 47 corresponds to cows treated twice, as they were refractory to the first treatment.
Figure 9B:
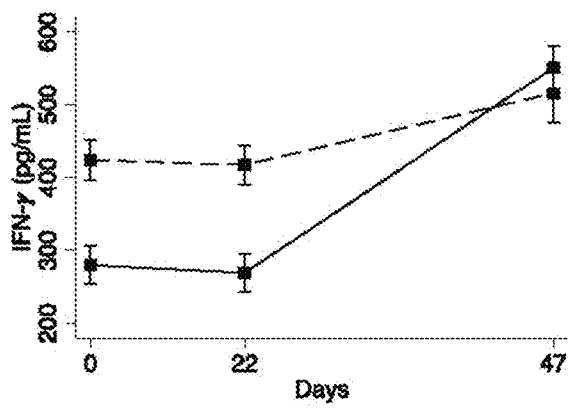
Figure 9C:
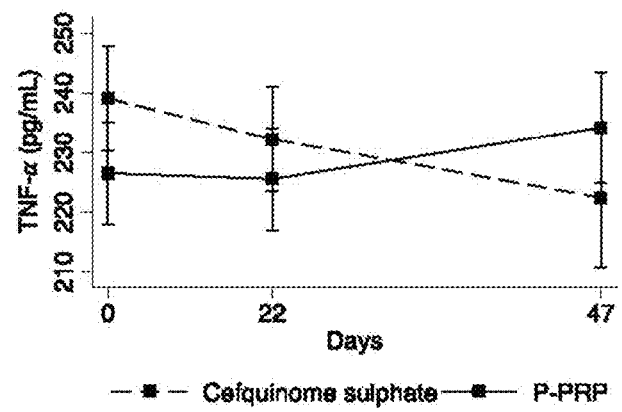

Concentrations of milk cytokines were measured at days 0 and 22 in cows treated once, and at days 0, 22, and 47 in cows treated twice. As shown in FIGS. 8A-8D, linear regression models showed a significant interaction between time and treatment for IL-1 (FIG. 8A), IL-2 (FIG. 8B) and IL-6 (FIG. 8D), while there were no differences observed between time and treatment (EG vs. RG) for IL-4 (FIG. 8C). Notably, concentrations of IL-1 and IL-2 increased in cows that were treated twice, the milk concentrations of these cytokines being highest at day 47 (FIGS. 8A and 8B). Furthermore, as shown in FIGS. 9A-9B, interaction between time and treatment (EG vs. RG) was significant for three additional cytokines: IL-8, IFN-γ, and IFN-α. The concentration of IFN-γ was higher in the RG on days 0 and 22, but increased in both groups (EG and RG) by day 47 in cows treated twice, without any differences being observed between the group on this day.

What is claimed is:

1. A pure platelet-rich plasma (P-PRP) injectable composition for intra-mammary injection comprising:
   bovine live platelets in a concentration of $250\text{-}800\times10^3$ platelets/µL;
   bovine plasma;
   an anticoagulant in a ratio of 0.5-2:10 by weight of the composition;
   calcium gluconate in a ratio of from 0.5:5 to 1:15 by weight of the composition; and
   extracellular proteins PF-4 and C3, wherein PF-4 is present in a concentration of $6\text{-}20\times10^3$ pg/mL, and C3 is present in a concentration of $40\text{-}80\times10^3$ pg/mL.

2. The P-PRP composition according to claim 1, wherein the bovine plasma is obtained from whole blood of a healthy bovine of the Blanco-Orejinegro breed.

3. The P-PRP composition according to claim 1, wherein the anticoagulant is CPDA-1.

4. A process for preparing a pure platelet-rich plasma (P-PRP) injectable composition, for intra-mammary injection comprising:
   extracting a sample of blood from a bovine;
   collecting the blood sample in a bag with an anticoagulant additive;
   subjecting the mixture to a single centrifugation cycle; and
   mixing the P-PRP composition with an activating substance calcium gluconate to induce platelet release or proteins and clot formation;
   wherein the process results in the P-PRP composition having a concentration of platelets of $250\text{-}800\times10^3$ platelets/µL, extracellular proteins PF-4 in a concentration of $6\text{-}20\times10^3$ pg/mL, and C3 in a concentration of $40\text{-}80\times10^3$ pg/mL, for treating subclinical mastitis caused by Gram-positive bacteria in a bovine.

5. The process of claim 4, wherein the single centrifugation cycle comprises centrifuging the mixture of the bags at 600-900 g for 1-12 minutes at 4-22° C.

6. The process of claim 4, further comprising storing the P-PRP composition under refrigerated conditions for up to 96 hours prior to mixing of the composition with the calcium gluconate.

7. A method for treating or preventing subclinical mastitis caused by Gram-positive bacteria in a mammal, comprising:
   administering to the mammal a therapeutically effective amount of the P-PRP injectable composition for intra-mammary injection of claim 1.

8. The method according to claim 7, wherein the P-PRP injectable composition is administered to a mammary organ of the mammal.

9. The method according to claim 7, further comprising continuing to administer additional therapeutically effective amounts of the P-PRP injectable composition for intra-mammary injection to the mammal throughout treatment periods, wherein the treatment period ranges from 24-96 hours, and the therapeutically effective amount of the P-PRP injectable composition is administered every 12 hours.

10. A kit for intramammary administration of an injectable pure platelet-rich plasma (P-PRP) composition, comprising:
   A) a pure platelet-rich plasma (P-PRP) injectable composition, comprising:
      bovine live platelets in a concentration of $250\text{-}800\times10^3$ platelets/µL;
      bovine plasma;
      CPDA-1 in a ratio of 0.5-2:10 by weight of the composition; and
   B) a sterile reaction tube containing calcium gluconate in a ratio of from 0.5:5 to 1:15 by weight of the composition.

11. A pure platelet-rich plasma (P-PRP) injectable composition for intra-mammary injection, according to claim 1 for use in the treatment or prevention of subclinical mastitis caused by Gram-positive bacteria in a mammal.

\* \* \* \* \*